United States Patent [19]
Saito

[11] Patent Number: 5,772,687
[45] Date of Patent: *Jun. 30, 1998

[54] HUB FOR SYRINGE, CONNECTING STRUCTURE OF HUB, SYRINGE, SYRINGE ASSEMBLY AND METHOD OF ASSEMBLING SYRINGE ASSEMBLY

[76] Inventor: Yoshikuni Saito, Ooaza Kitanogami 1930, Kurobanemachi, Nasu-gun, Tochigi-Ken, Japan

[ * ] Notice: The term of this patent shall not extend beyond the expiration date of Pat. No. 5,716,341.

[21] Appl. No.: 531,670

[22] Filed: Sep. 21, 1995

Related U.S. Application Data

[63] Continuation of Ser. No. 213,434, Mar. 14, 1994, abandoned.

[30] Foreign Application Priority Data

| Mar. 12, 1993 | [JP] | Japan | ................................ 5-79184 |
| Apr. 6, 1993 | [JP] | Japan | ............................. 5-103527 |

[51] Int. Cl.⁶ .............................. A61M 5/00; A61M 5/31
[52] U.S. Cl. ......................... 604/243; 604/110; 604/195; 604/228; 604/240
[58] Field of Search .................................... 604/110, 195, 604/196, 218, 227–229, 240, 242, 243, 181, 187, 241

[56] References Cited

U.S. PATENT DOCUMENTS

| 3,848,593 | 11/1974 | Baldwin | ................................. 604/242 |
| 4,675,005 | 6/1987 | DeLuccia | ................................ 604/110 |
| 4,692,156 | 9/1987 | Haller | .................................... 604/195 |
| 4,710,170 | 12/1987 | Haber et al. | ........................... 604/110 |

(List continued on next page.)

FOREIGN PATENT DOCUMENTS

| 0364387 | 4/1990 | European Pat. Off. . |
| 9215295 | 10/1992 | Germany . |
| 178348 | 11/1986 | Japan . |
| 2357 | 1/1988 | Japan . |
| 107382 | 4/1988 | Japan . |
| 503456 | 4/1988 | Japan . |
| 144125 | 6/1988 | Japan . |
| 506068 | 7/1988 | Japan . |
| 219534 | 9/1988 | Japan . |
| 317634 | 12/1988 | Japan . |
| 7522 | 1/1989 | Japan . |
| 25601 | 2/1989 | Japan . |
| 94284 | 4/1989 | Japan . |
| 165147 | 6/1989 | Japan . |
| 201506 | 8/1989 | Japan . |
| 508739 | 8/1989 | Japan . |
| 500795 | 12/1989 | Japan . |
| 62155 | 6/1990 | Japan . |
| 509324 | 7/1990 | Japan . |
| 238860 | 9/1990 | Japan . |
| 256678 | 9/1990 | Japan . |
| 401754 | 12/1990 | Japan . |
| 41240 | 2/1991 | Japan . |
| 8900432 | 1/1989 | WIPO . |
| 8909075 | 10/1989 | WIPO . |
| 9209320 | 6/1992 | WIPO . |
| 9211883 | 7/1992 | WIPO . |
| 9218186 | 10/1992 | WIPO | ................................... 604/195 |

*Primary Examiner*—Michael Powell Buiz
*Assistant Examiner*—Ronald K. Stright
*Attorney, Agent, or Firm*—Eckert Seamans Cherin & Mellott

[57] ABSTRACT

A hub to be attachably and detachably inserted into a hub insertion hole of a syringe body having a hub insertion hole cylindrically formed at a top thereof has a cylindrical hub body through which the hub can be inserted into the hub insertion hole and can be pulled out of the hub insertion hole in a syringe body. At an outer peripheral portion of the hub body, a hub stop groove in the shape of a groove is annularly formed capable of engaging with the hub stop rib. At an end face of the hub body, a needle insertion hole capable of inserting a needle therein is provided. A flow hole is provided with the hub body such that the needle insertion hole communicates with the inside of the syringe body. At an end face of the hub body, a piston engagement hole is provided so as to engage with the piston.

15 Claims, 18 Drawing Sheets

U.S. PATENT DOCUMENTS

| | | | |
|---|---|---|---|
| 4,900,304 | 2/1990 | Fujioka et al. | 604/242 |
| 4,941,883 | 7/1990 | Venturini | 604/186 |
| 4,950,241 | 8/1990 | Ranford | 604/110 |
| 4,955,870 | 9/1990 | Ridderheim et al. | 604/198 |
| 5,026,354 | 6/1991 | Kocses | 604/195 |
| 5,098,402 | 3/1992 | Davis | 604/195 |
| 5,112,316 | 5/1992 | Venturini | 604/195 |
| 5,205,824 | 4/1993 | Mazur . | |
| 5,273,538 | 12/1993 | Chen | 604/195 |
| 5,308,329 | 5/1994 | Mazur et al. | 604/110 |

5,772,687

HUB FOR SYRINGE, CONNECTING STRUCTURE OF HUB, SYRINGE, SYRINGE ASSEMBLY AND METHOD OF ASSEMBLING SYRINGE ASSEMBLY

This is a continuation of U.S. application Ser. No. 08/213,434, filed on Mar. 14, 1994, now abandoned.

BACKGROUND OF THE INVENTION

This invention relates to a hub for a syringe, connecting structure of the hub, the syringe, a syringe assembly and a method of assembling the syringe assembly, suitable for applying to a throwaway syringe assembly.

Since patient's blood included pathogenic bacteria adheres to a needle of a syringe assembly used, many throwaway syringe assemblies have been used for preventing secondary infection.

A conventional throwaway syringe assembly is disposed so as to discard after use. However, since it is necessary to remove a danger of secondary infection generating through the wound of a hand or the like by a needle attached a patient's blood and the like thereto when the needle is dealt with, the needle is cut from the syringe assembly with scissors or the like after use, and after that, they are discarded.

However, the handling operation of a conventional throwaway syringe assembly requires a long time since it is necessary to handle it with religious care so as not to hurt a hand or the like with the needle just after its use till the needle is cut.

In addition, the cutting operation of a conventional throwaway syringe assembly to be executed before disposal is troublesome.

Then, the throwaway syringe assembly, capable of maintaining safety just after use by inserting a needle into a syringe of the syringe assembly just after use, and omitting cutting operation of a needle, has been proposed. However, the assembly and the operation of the proposed syringe assembly are difficult since its structure is complex.

An object of the present invention is to provide a hub for a syringe, connecting structure of the hub, the syringe, a syringe assembly and a method of assembling the syringe assembly, in a throwaway syringe assembly, with which safety of the operations can be maintained just after use till its disposal and its disposal operation does not require a long time, and its assembly and operation is easy, taking the above-mentioned circumstances into consideration.

SUMMARY OF THE INVENTION

Of the present invention the 1st invention comprises a hub for a syringe assembly, said syringe assembly having a syringe body slidably attached a piston thereto, said syringe body having a hub insertion hole cylindrically formed through a needle guide hole at a top thereof, said hub to be attachably and detachably attached to said hub insertion hole comprising:

a cylindrical hub body through which said hub is inserted into said hub insertion hole and is pulled out of said hub insertion hole in said syringe body;

a seal portion annularly formed at an outer peripheral portion of said hub body capable of engaging with an inner face of said hub insertion hole;

a needle insertion hole capable of inserting a needle therein provided at one end of said hub body in a direction of an axis center of said hub body; and a hub side engagement means capable of engaging with said piston provided at the other end of said hub body.

With this invention, the hub body and the hub insertion hole are contacted with each other through the seal portion, thereby the portion between both are firmly sealed. It is possible to provide the hub, which is easily attached to and detached from the hub insertion hole, by which a predetermined sealing efficiency can be exercised. In case of assembling, the operation of disposing the hub and the operation of pulling a needle into the syringe after its use can be easily and smoothly executed.

Of the present invention, the 2nd invention comprises the hub for the syringe assembly in the 1st invention, wherein said needle insertion hole communicates and contacts with said other end of said hub body.

With this invention, the needle insertion hole communicates with the other end of the hub body.

Of the present invention, the 3rd invention comprises the hub for the syringe assembly in the 1st invention, wherein said hub side engagement means communicates with said needle insertion hole.

With this invention, the needle insertion hole communicates with the hub side engagement means.

Of the present invention, the 4th invention comprises the hub for the syringe assembly in the 1st invention, wherein an outside diameter of parts excluding said seal portion of said hub body is smaller than an inside diameter of corresponding parts of said hub insertion hole.

Therefore, the hub can be contacted with the hub insertion hole only through the seal portion. It is possible to provide the hub, which is easily attached to and detached from the hub insertion hole, by which a predetermined sealing efficiency can be exercised. In case of assembling, the operation of disposing the hub and the operation of pulling a needle into the syringe after its use can be easily and smoothly executed. Of the present invention, the 5th invention comprises the hub in the 1st invention, wherein said seal portion is formed in the shape of a groove.

With the invention, in addition to the effects of the 1st invention, the insertion and disposal of the hub into the hub insertion hole is made easier since no projection is formed on the hub outer peripheral portion.

Of the present invention, the 6th invention comprises the hub in the 1st invention, wherein said seal portion is formed in the shape of a projection.

With this invention, in addition to the effects of the 1st invention, the sealing efficiency of the hub can be controlled at the hub side by arranging various kinds of formations of the projection. It is possible to provide the hub according to the use of a syringe assembly.

Of the present invention, the 7th invention comprises a structure of connecting a hub in which a hub for a syringe assembly is attachably and detachably connected with a syringe having a syringe body formed a hub insertion hole at a top thereof through a needle guide hole, said structure of connecting said hub comprising:

said hub body of said hub of the 1st invention attachably and detachably inserted in said hub insertion hole so as to be inserted into said hub insertion hole and be pulled out of said hub insertion hole in said syringe body; and a hub seal portion annularly provided at an inner peripheral face of said hub insertion hole and said seal portion of said hub body provided so as to contact and engage with said hub seal portion with a predetermined contact pressure.

Of the present invention, the 8th invention comprises a structure of connecting a hub in which a hub for a syringe assembly is attachably and detachably connected with a syringe having a syringe body formed a hub insertion hole at a top thereof through a needle guide hole, said structure of connecting said hub comprising:

said hub body of said hub of the 5th invention attachably and detachably inserted in said hub insertion hole so as to be inserted into said hub insertion hole and be pulled out of said hub insertion hole in said syringe body; and a hub seal portion provided in the shape of annular projection at an inner peripheral face of said hub insertion hole and said seal portion of said hub body provided so as to contact and engage with said hub seal portion with a predetermined contact pressure.

Of the present invention, the 9th invention comprises a structure of connecting a hub in which a hub for a syringe assembly is attachably and detachably connected with a syringe having a syringe body formed a hub insertion hole at a top thereof through a needle guide hole, said structure of connecting said hub comprising:

said hub body of said hub of the 6th invention attachably and detachably inserted in said hub insertion hole so as to be inserted into said hub insertion hole and be pulled out of said hub insertion hole in said syringe body; and a hub seal portion provided in the shape of annular groove at an inner peripheral face of said hub insertion hole and said seal portion of said hub body provided so as to contact and engage with said hub seal portion with a predetermined contact pressure.

With these the 7th, the 8th and the 9th inventions, the hub body and the hub insertion hole are contacted with each other through the seal portion, thereby the portion between both are firmly sealed. It is possible to provide the connecting structure of the hub, which is easily attached to and detached from the hub insertion hole, by which a predetermined sealing efficiency can be exercised. In case of assembling, the operation of disposing the hub and the operation of pulling a needle into the syringe after its use can be easily and smoothly executed.

Of the present invention, the 10th invention comprises the structure of connecting the hub in the 8th or the 9th invention, wherein a width of said seal portion is different from one of said hub seal portion.

With the invention, when the seal portion and the hub seal portion are engaged with each other, the contacting portion can be made point contact state in the section in the direction of the axis of the hub. Therefore, high sealing efficiency can be exercised in comparison with sealing with face contact.

Of the present invention, the 11th invention comprises a structure of connecting a hub in which a hub for a syringe assembly is attachably and detachably connected with a syringe having a syringe body formed a hub insertion hole at a top thereof through a needle guide hole, said structure of connecting said hub comprising:

said hub body of said hub of the 6th invention attachably and detachably inserted in said hub insertion hole so as to be inserted into said hub insertion hole and be pulled out of said hub insertion hole in said syringe body; and a hub seal portion provided on the same face as an inner peripheral face of said hub insertion hole and said seal portion of said hub body provided so as to contact and engage with said hub seal portion with a predetermined contact pressure.

With this invention, the hub body and the hub insertion hole are contacted with each other through the seal portion, thereby the portion between both are firmly sealed. It is possible to provide the structure of connecting the hub, which is easily attached to and detached from the hub insertion hole, by which a predetermined sealing efficiency can be exercised. In case of assembling, the operation of disposing the hub and the operation of pulling a needle into the syringe after its use can be easily and smoothly executed.

Of the present invention, the 12th invention comprises the structure of connecting the hub in the 7th, the 8th, the 9th or the 11th invention, wherein a gap is formed between said inner peripheral face of said hub insertion hole excluding said hub seal portion and said outer peripheral face of said hub body.

With this invention, the hub and the hub insertion hole inner peripheral face are contacted with each other only through the seal portion and the hub seal portion. Attachment and detachment of the hub to the hub insertion hole can be extremely easily executed, and the assembly operation of a syringe assembly can be efficiently easily executed. In addition, since the contact between the hub and the inner peripheral face are only the seal portion and the hub seal portion, the hub can be retracted into the inside of the syringe assembly with small retracting force when a needle used is retracted into the inside of a syringe assembly. And then, disposal operation of a syringe assembly used can be smoothly and easily executed.

Of the present invention, the 13th invention comprises the structure of connecting the hub in the 7th, the 8th, the 9th or the 11th invention, wherein said hub body is inserted in said hub insertion hole from said needle guide hole side.

With this invention, in addition to the effects of the respective inventions, insertion of the hub can be executed in such a state that the piston is inserted into the syringe body. It is possible to reduce the possibility of entering dust into the syringe body at the time of insertion of the hub, so it is hygienic.

Of the present invention, the 14th invention comprises the structure of connecting the hub in the 7th, the 8th, the 9th or the 11th invention, wherein one or more slits are formed at a periphery of said needle guide hole of said syringe body.

With this invention, the hub can be easily inserted from the hub insertion hole side making use of elastic deformation of the slits. In addition, insertion of the hub can be executed in such a state that the piston is inserted into the syringe body. It is possible to reduce the possibility of entering dust into the syringe body at the time of insertion of the hub, so it is hygienic.

Of the present invention, the 15th, the 16th, the 17th and 18th inventions comprise a syringe assembly, comprising:

a syringe and a hub having the connecting structure of the 7th, the 8th, the 9th or the 11th invention,;

a piston provided with said syringe body occupying an inside of said syringe body in a direction of an axis so as to be movable in said direction of said axis with respect to said syringe body;

a piston side engagement means provided with said piston so as to engage with said hub side engagement means of said hub, facing said hub side engagement means; and a needle provided in said needle insertion hole of said hub.

With these inventions, the hub is engaged with the piston side engagement means of the piston after use of the syringe assembly, thereby the hub can be pulled into the inside of the syringe with the needle, and the needle used can be easily pulled into the inside of the syringe with only the operation of pressing and pulling of the piston, the same as the case of operation of an usual syringe assembly. Therefore, its operation is easy for everybody, there is no danger of error operation, and high safety is secured.

Of the present invention, the 19th invention comprises the syringe assembly in the 16th or the 17th invention, wherein a width of said seal portion is different from one of said hub seal portion.

With the invention, when the seal portion and the hub seal portion are engaged with each other, the contacting portion can be made point contact state in the section in the direction of the axis of the hub. Therefore, high sealing efficiency can be exercised in comparison with sealing with face contact.

Of the present invention, the 20th invention comprises the syringe assembly in the 15th, the 16th, the 17th or the 18th invention, wherein said piston is comprised such that said piston body can be bent and taken between an operation portion and a liquid medicine press portion.

With this invention, the needle can remain in the inside of the syringe being held with the top end portion of the piston by bending and taking the piston, thereby it is not operable from the outside. High safety is secured in case of disposal operation after that.

Of the present invention, the 21st invention comprises the syringe assembly in the 20th invention, wherein a piston stopper is provided with said syringe body so as not to pull said liquid medicine press portion of said piston out of said syringe body.

With this invention, it is possible to prevent an operator from hurting with the needle used by inadvertently pulling the piston out of the syringe body when the piston is moved together with the needle. Therefore, high safety is secured.

Of the present invention, the 22nd and the 23rd inventions comprise the syringe assembly in the 20th or the 21st invention, wherein a notch for bending and taking is formed at said piston body of said piston.

With this invention, the operation of bending and taking of the piston can be executed by making use of the notches.

Of the present invention, the 24th invention comprises the syringe assembly in the 23rd invention, wherein said notch is formed so as to position at end portion of said syringe body when said piston abuts on said piston stopper.

With this invention, the piston is pulled till it abuts on the piston stopper, and after that, the piston can be immediately bend and taken by making use of its end portion, and the operation of storing and remaining the needle in the syringe can be successively executed. Therefore, the operations of injection and disposal can be effectively executed.

Of the present invention, the 25th invention comprises a method of assembling a syringe assembly in case of assembly of the syringe assembly of the 15th, the 16th, the 17th or the 18th invention, said method of assembling said syringe assembly comprising;

inserting said hub into said hub insertion hole from a side where said piston is inserted of said syringe body;

disposing said hub so as to elastically engage said seal portion of said hub with said hub seal portion of said hub insertion portion;

inserting said piston into said syringe; and inserting and connecting said needle into and with said needle insertion hole of said hub.

With this invention, assembly inserting the hub from the piston insertion side can be executed.

Of the present invention, the 26th invention comprises a method of assembling a syringe assembly in case of assembly of the syringe assembly of the 15th, the 16th, the 17th or the 18th invention, said method of assembling said syringe assembly comprising:

inserting said piston into said syringe;

inserting said hub into said hub insertion hole from said needle guide hole side of said syringe body;

disposing said hub so as to elastically engage said seal portion of said hub with said hub seal portion of said hub insertion portion; and inserting and connecting said needle into and with said needle insertion hole of said hub.

With this invention, insertion of the hub can be executed in such a state that the piston is inserted into the syringe body. It is possible to reduce the possibility of entering dust into the syringe body at the time of insertion of the hub, so it is hygienic.

Of the present invention, the 27th invention comprises a method of assembling a syringe assembly in case of assembly of the syringe assembly of the 15th, the 16th, the 17th or the 18th invention, said method of assembling said syringe assembly comprising:

inserting said piston into said syringe;

inserting said hub attached said needle thereto into said hub insertion hole from said needle guide hole side of said syringe body; and disposing said hub so as to elastically engage said seal portion of said hub with said hub seal portion of said hub insertion portion.

With this invention, insertion of the hub can be executed in such a state that the piston is inserted into the syringe body. It is possible to reduce the possibility of entering dust into the syringe body at the time of insertion of the hub, so it is hygienic. In addition, when the hub is inserted in the hub insertion hole, extra operation of insertion of the needle in the syringe assembled can be avoided since the needle has already been inserted into the hub. Therefore, the assembly operation can be quickly executed.

Of the present invention, the 28th invention comprises a method of assembling a syringe assembly in case of assembly of the syringe assembly of the 15th, the 16th, the 17th or the 18th invention, said method of assembling said syringe assembly comprising:

forming one or more slits at a periphery of said needle guide hole of said syringe body;

inserting said piston into said syringe;

inserting said hub attached said needle thereto into said hub insertion hole from said needle guide hole side of said syringe body; and disposing said hub so as to elastically engage said seal portion of said hub with said hub seal portion of said hub insertion portion.

With this invention, insertion of the hub can be executed in such a state that the piston is inserted into the syringe body. It is possible to reduce the possibility of entering dust into the syringe body at the time of insertion of the hub, so it is hygienic. In addition, when the hub is inserted in the hub insertion hole, extra operation of insertion of the needle in the syringe assembled can be avoided since the needle has already been inserted into the hub. Therefore, the assembly operation can be quickly executed. In addition, since the hub can be easily inserted from the hub insertion hole side by making use of elastic deformation of the slits, the insertion operation of the hub can be quickly and easily executed.

Of the present invention, the 29th invention comprises a method of assembling a syringe assembly in case of assembly of the syringe assembly of the 15th, the 16th, the 17th or the 18th invention, said method of assembling said syringe assembly comprising:

forming one or more slits at a periphery of said needle guide hole of said syringe body;

inserting said piston into said syringe;

inserting said hub into said hub insertion hole from said needle guide hole side of said syringe body;

disposing said hub so as to elastically engage said seal portion of said hub with said hub seal portion of said hub insertion portion; and inserting and connecting said needle into and with said needle insertion hole of said hub.

With this invention, insertion of the hub can be executed in such a state that the piston is inserted into the syringe body. It is possible to reduce the possibility of entering dust into the syringe body at the time of insertion of the hub, so it is hygienic. In addition, since the hub can be easily inserted from the hub insertion hole side by making use of elastic deformation of the slits, the insertion operation of the hub can be quickly and easily executed.

Of the present invention, the 30th invention comprises a syringe comprising:

a syringe body formed a liquid medicine injection space therein;

a piston provided with said syringe body being slidably in a direction of an axis center of said syringe body;

a hub insertion hole formed at top of said syringe body communicating with said liquid medicine injection space;

a needle guide hole provided at top of said hub insertion hole so as to communicate said hub insertion hole with an outside; and one or more slits formed at a periphery of said needle guide hole.

With this invention, the insertion operation of the hub can be easily executed since the hub is inserted from the needle guide hole side by making use of elastic deformation of the slits when the hub is inserted in the syringe body. In addition, entering dust into the syringe body is extremely saved and it is hygienic since the insertion of the hub can be executed in such a state that the piston is inserted in the syringe body.

Of the present invention, the 31st invention comprises the syringe in the 30th invention, wherein a hub seal portion is annularly formed at an inner peripheral face of said hub insertion hole.

With this invention, the syringe body can be contacted with the hub only through the hub seal portion. It is possible to provide the syringe, in which the hub is easily attached to and detached from the hub insertion hole, by which a predetermined sealing efficiency can be exercised between the syringe body and the hub. In case of assembling, the operation of inserting the hub and the operation of pulling a needle into the syringe after its use can be easily and smoothly executed.

Of the present invention, the 32nd invention comprises the syringe in the 31st invention, wherein said hub seal portion is comprised of a groove annularly formed.

With the invention, the insertion and installment of the hub into the hub insertion hole is made easier since no projection is formed on the inner peripheral portion of the hub insertion hole.

Of the present invention, the 33rd invention comprises the syringe in the 31st invention, wherein said hub seal portion is comprised of a projection annularly formed.

With this invention, the sealing efficiency between the hub insertion hole and the hub can be controlled at the syringe side by arranging various kinds of formations of the projection. It is possible to provide the syringe according to the use of a syringe assembly.

Of the present invention, the 34th invention comprises the syringe in the 30th invention, wherein a piston side engagement means is provided with a liquid medicine press portion of a top of said piston being capable of engaging with said hub to be inserted into said hub insertion hole.

With the invention, the piston side engagement means is engaged with the hub after use of the syringe assembly, thereby the hub can be pulled into the inside of the syringe with the needle, and the syringe assembly used can be easily pulled into the inside of the syringe with only the operation of pressing and pulling of the piston, the same as the case of operation of an usual syringe assembly. Therefore, its operation is easy for everybody, there is no danger of error operation, and high safety is secured.

Of the present invention, the 35th invention comprises the syringe in the 34th invention, wherein said piston is comprised such that a piston body can be bent and taken between an operation portion and said liquid medicine press portion.

With this invention, the needle can remain in the inside of the syringe being held with the top end portion of the piston by bending and taking the piston, thereby it is not operable from the outside. High safety is secured in case of disposal operation after that.

Of the present invention, the 36th invention comprises the syringe in the 35th invention, wherein a piston stopper is provided with said syringe body so as not to pull said liquid medicine press portion of said piston out of said syringe body.

With this invention, it is possible to prevent an operator from hurting with the needle used by inadvertently pulling the piston out of the syringe body when the piston is moved together with the needle. Therefore, high safety is secured.

Of the present invention, the 37th and the 38th inventions comprise the syringe in the 35th or the 36th invention, wherein a notch for bending and taking is formed at said piston body of said piston.

With these inventions, the operation of bending and taking of the piston can be easily executed by making use of the notches.

Of the present invention, the 39th invention comprises the syringe for a syringe assembly in the 38th invention, wherein said notch is formed so as to position at end portion of said syringe body when said piston abuts on said piston stopper.

With this invention, the piston is pulled till it abuts on the piston stopper, and after that, the piston can be immediately bent and taken by making use of its end portion, and the operation of storing and remaining the needle in the syringe can be successively executed. Therefore, the operations of injection and disposal can be effectively executed.

DESCRIPTION OF THE PREFERRED EMBODIMENT

Embodiments Of the present invention will now be described hereinafter with respect to the accompanying drawings.

Figure 1:
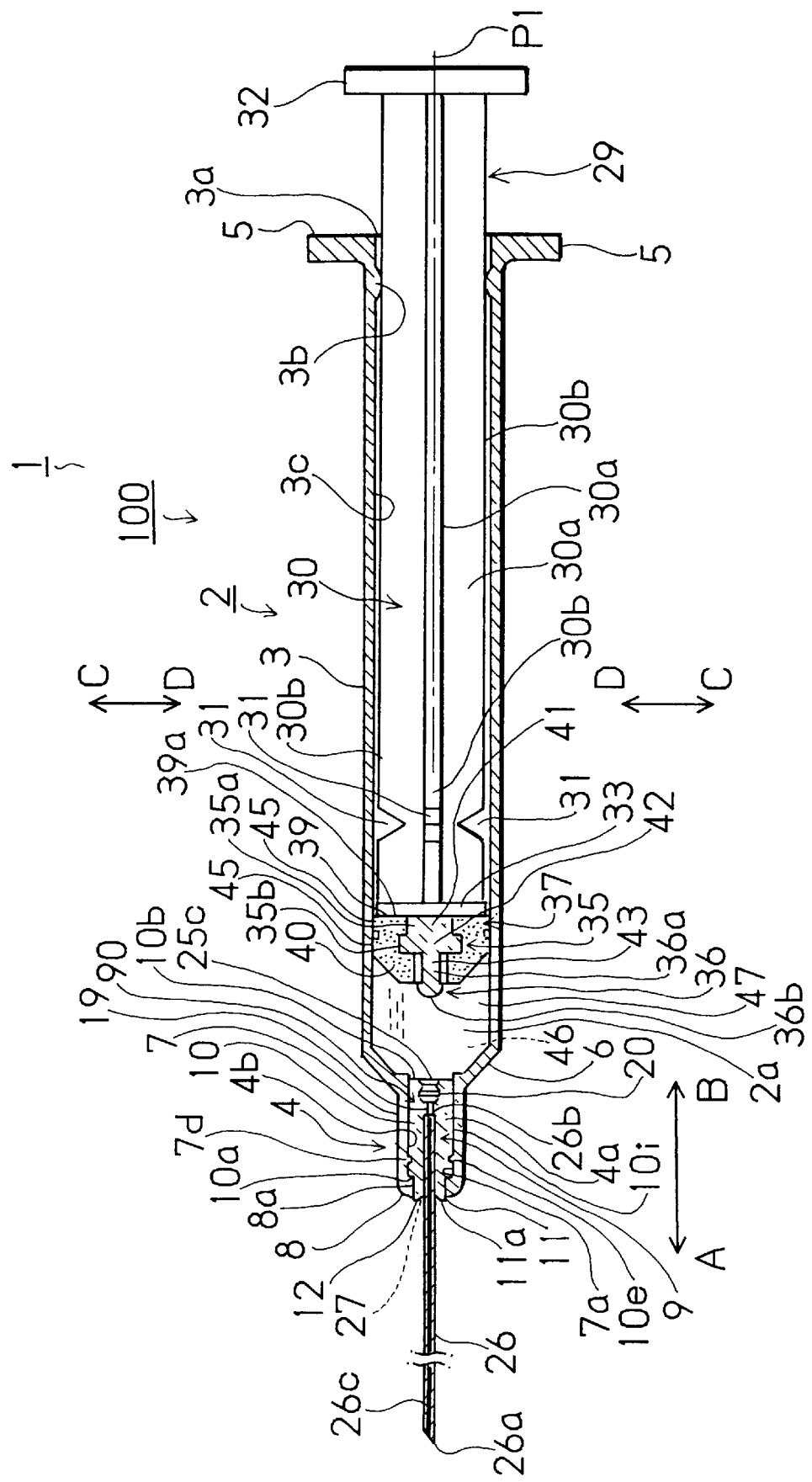
FIG. 1 is a typical sectional view showing an example of a syringe assembly according to the present invention.

A syringe assembly 1 according to the present invention has a syringe 100 made of resin, as shown in FIG. 1. A syringe body 2 is provided with the syringe 100 (FIG. 1 is a typical cross section of the syringe assembly 1, but its side is shown in a part of a piston 29, described hereinafter, not the section, for convenience.). A main cylindrical portion 3, cylindrically formed, is provided with the syringe body 2. A direction of an axis center of the main cylindrical portion 3, that is, the reciprocating directions parallel to an axis center P1 are A direction in the figure (or the left direction of the paper of FIG. 1) and B direction (or the right direction of the paper of FIG. 1).

At the outer periphery side of the main cylindrical portion 3, a syringe support 5, being in the shape of a plate, is provided near an opening end 3a of the arrow B side of the main cylindrical portion 3 (the right side of the paper of FIG. 1), in such a manner as forming a flange of the main cylindrical portion 3. Both plate faces of the syringe support 5 are perpendicular to the directions as shown by the arrows A and B. At an inner peripheral face 3c side of the main cylindrical portion 3, an engagement rib 3b, projecting in the direction for the axis center P1 of the main cylindrical portion 3, that is, the direction as shown by an arrow D, is annularly formed near the opening end 3a along the inner peripheral face 3c.

At the arrow A side of the main cylindrical portion 3 (the left side of the paper of FIG. 1) a taper 6 in the shape of a funnel is formed unitedly connecting with the main cylindrical portion 3. The inside diameter in the section perpendicular to the directions as shown by the arrows A and B of the taper 6 (that is, the circular section) is made narrower for the direction as shown by the arrow A.

The inside of the main cylindrical portion 3 and the inside of the taper 6 communicate with each other in the directions as shown by the arrows A and B, and the space combined both insides is an inside space 2a of the syringe body 2.

Figure 2:
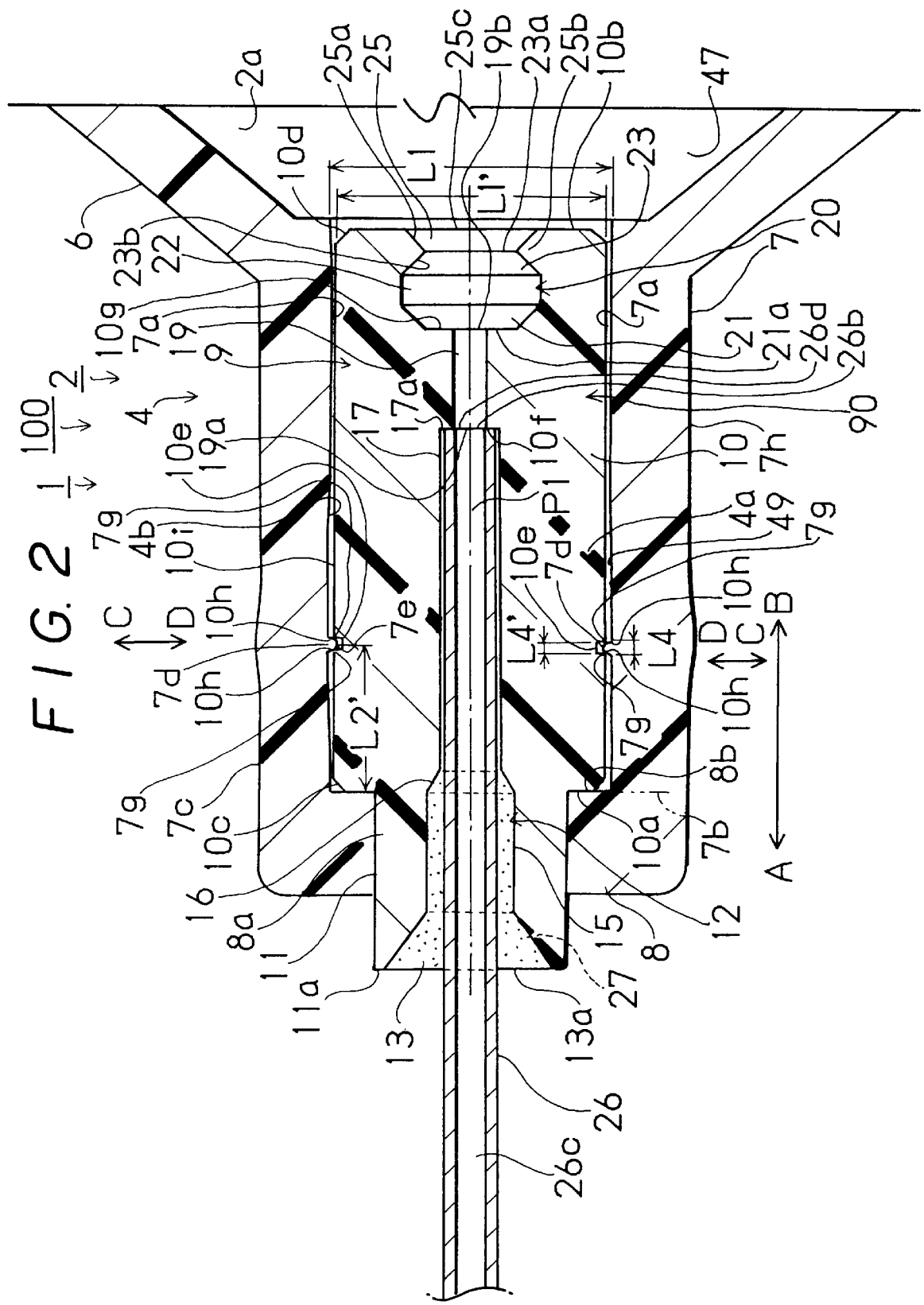
FIG. 2 is an enlarged sectional view in a portion near a hub of the syringe assembly as shown in FIG. 1.

At the side of the arrow A of the taper 6, that is, at the side of the top of the syringe body 2, as shown in FIGS. 1 and 2, a hub insertion portion 4 is formed unitedly connecting with the taper 6, and is elastically deformed. A hub 9 made of resin, which is harder than the syringe 100, is provided with a hub insertion hole 4b of the hub insertion portion 4 elastically deformed.

Prior to the explanation of the hub insertion portion 4 elastically deformed, the hub insertion portion 4 in its natural form, which is not elastically deformed, and the hub 9 will now be respectively explained.

Figure 3:
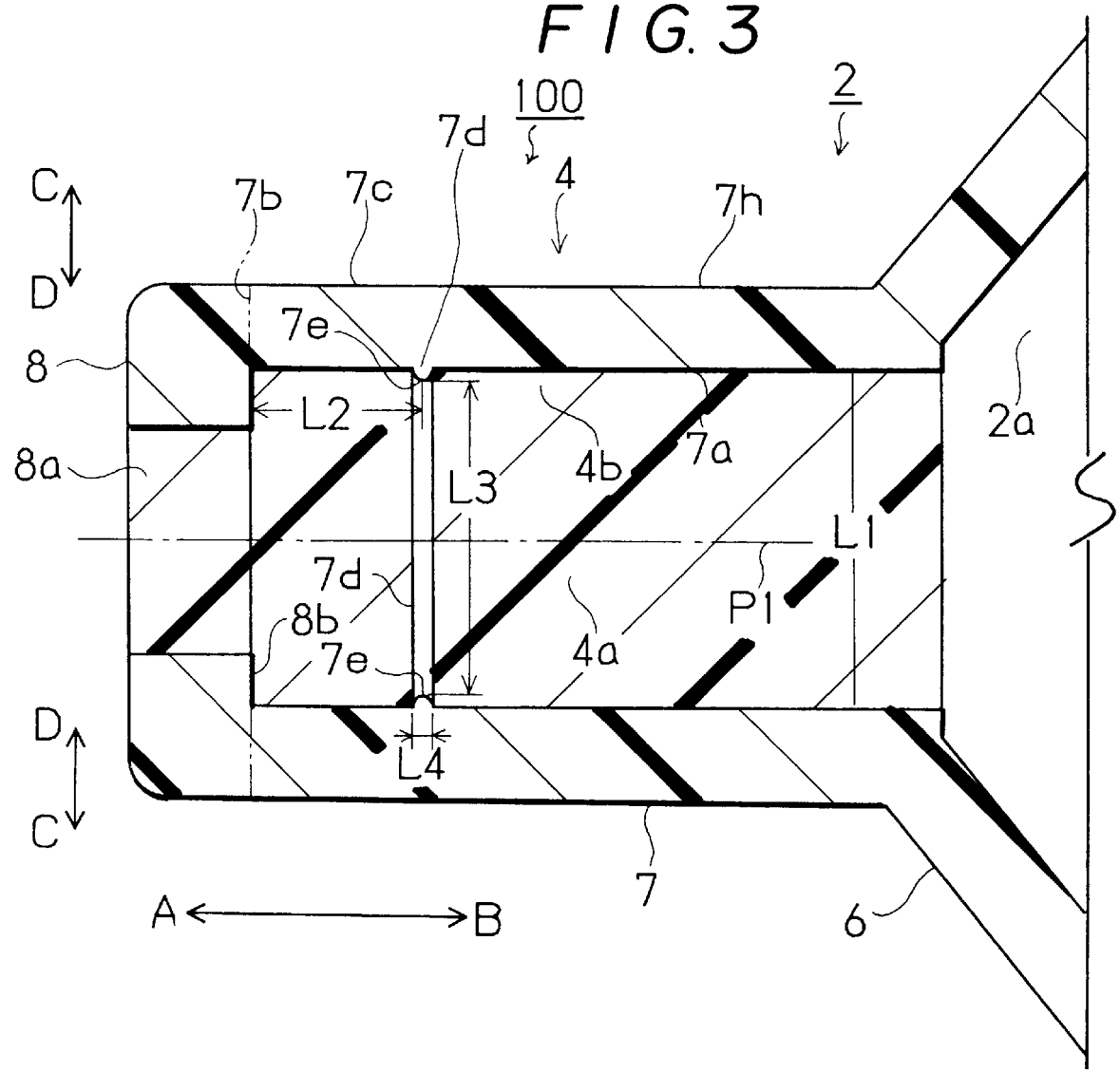
FIG. 3 is a view showing a portion near a hub insertion portion as shown in FIG. 2 in a natural state.

The hub insertion portion 4, which is not elastically deformed, as shown in FIG. 3, has a small cylindrical portion 7. The small cylindrical portion 7 is formed unitedly connecting with the taper 6. That is, the hub insertion portion 4 is formed unitedly connecting with the taper 6 in the small cylindrical portion 7. The small cylindrical portion 7 is formed coaxially with the main cylindrical portion 3. An inside diameter L1 of the small cylindrical portion 7 is smaller than one of the main cylindrical portion 3(The inside diameter L1 of the small cylindrical portion 7 means one in the part where a hub stop rib 7d described hereinafter is not formed, of the inside diameter of the small cylindrical portion 7).

An inner peripheral face 7a side of the small cylindrical portion 7 is the hub insertion hole 4b. The hub stop rib 7d is formed in the hub insertion hole 4b, projecting for the axis center P1. The hub stop rib 7d is formed along the inner peripheral face 7a of the small cylindrical portion 7, along the circumference which center is the axis center P1, that is, annularly. Of the inside diameter of the small cylindrical portion 7, the inside diameter in a top end 7e of the hub stop rib 7d is L3, and the width of the hub stop rib 7d in the directions as shown by the arrows A and B is width L4. The section of a flat surface including the axis center P1 of the hub stop rib 7d (that is, the section as shown in FIG. 3) is circular arc.

An end wall 8, being in the shape of a circular plate, is formed at the small cylindrical portion 7 such that the outside diameter of the end wall 8 is equal to one of the small cylindrical portion 7 and both front and back wall surfaces thereof are perpendicular to the directions as shown by the arrows A and B. The end wall 8 is provided being united with the small cylindrical portion 7 in such a manner that a wall face 8b of the end wall 8 at the arrow B side and an end portion 7b of the small cylindrical portion 7 at the arrow A side are in contact with each other. A circular hole 8a, which center is the axis center P1, is provided with the end wall 8 penetrating both front and back wall faces of the end wall 8 in the directions as shown by the arrows A and B.

Of the small cylindrical portion 7, the distance between the end portion 7b and the hub stop rib 7d in the directions as shown by the arrows A and B is L2. The portion corresponding to the distance L2 of the small cylindrical portion 7 (that is, the cylindrical portion) is an extendable portion 7c. The inside of the small cylindrical portion 7, that is, the inside of the hub insertion hole 4b is a hub insertion space 4a.

The hub insertion portion 4 in a natural state which is not elastically deformed is comprised as explained hereinbefore. The syringe 100 is comprised such that the syringe body 2 and syringe support 5 are unitedly formed with each other. The syringe body 2 is comprised such that the main cylindrical portion 3, the taper 6, the hub insertion portion 4 are unitedly formed with one another.

On the other hand, the hub 9 has a hub body 90 as shown in FIG. 2. A main pillar portion 10, which longitudinal direction is parallel to the directions as shown by the arrows A and B, being in the shape of a cylinder which axis center is the axis center P1, is provided with the hub body 90. An outside diameter L1' of the main pillar portion 10 is smaller than the inside diameter L1 of the small cylindrical portion 7 in a natural state in the portion where no hub stop rib 7d exists, and is bigger than the inside diameter L3 in the top end 7e of the hub stop rib 7d of the small cylindrical portion 7. Chamfer portions 10c, 10d, in the shape of a taper, are respectively formed at the corner of the outer peripheral end side in an end face 10a of the main pillar portion 10 at the arrow A side (the left side of the paper of FIG. 2) and the corner of the outer peripheral end side in an end face 10b of the main pillar portion 10 at the arrow B side (the right side of the paper of FIG. 2).

A hub stop groove 10e is formed at the side of an outer peripheral face 10i of the main pillar portion 10. The hub stop groove 10e is annularly formed along the outer periphery side of the main pillar portion 10. The hub stop groove 10e is positioned at the position apart from the end face 10a of the main pillar portion 10 by a distance L2' in the direction as shown by the arrow B, and the distance L2' is slightly longer than the distance L2. Annular opening ends 10h, 10h are formed on the outer peripheral face 10i at the arrows A and B sides by provision of the hub stop groove 10e. A width L4' between the opening ends 10h and 10h in the directions as shown by the arrows A and B is narrower than the width L4 of the hub stop rib 7d of the small cylindrical portion 7.

A small pillar portion 11 is provided at the side of the end face 10a of the main pillar portion 10 extending in the directions as shown by the arrows A and B, being united with the main pillar portion 10, coaxial with the main pillar portion 10. The outside diameter of the small pillar portion 11 is smaller than the outside diameter L1' of the main pillar portion 10, and is slightly smaller than the inside diameter of the hole 8a provided on the end wall 8 of the small cylindrical portion 7 of the syringe body 2.

A needle insertion hole 12 is provided with the hub 9 as shown in FIG. 2. The needle insertion hole 12 is comprised of a first taper hole 13, a first cylindrical hole 15, a second taper hole 16 and a second cylindrical hole 17.

In the first taper hole 13, a circular opening 13a, which axis center is the axis center P1, is formed at an end face 11a of the small pillar portion 11 of the hub 9 at the arrow A side (the left side of the paper of FIG. 2), and the first taper hole 13 is formed orienting to the direction as shown by the arrow B from the end face 11a. The diameter of the section of the first taper hole 13 perpendicular to the directions as shown by the arrows A and B (that is, circular section which center is the axis center P1) is made narrower for the direction as shown by the arrow B.

The first cylindrical hole 15, in the shape of a cylinder, which center is the axis center P1, is provided with the hub 9 at the arrow B side of the first taper hole 13 (the right side of the paper of FIG. 2) connecting with the first taper hole 13.

The second taper hole 16 is provided with the hub 9 in the direction as shown by the arrow B at the arrow B side of the first cylindrical hole 15 connecting with the first cylindrical hole 15. The diameter of the section of the second taper hole 16 perpendicular to the directions as shown by the arrows A and B (the circular section which center is the axis center P1) is made narrower for the the direction as shown by the arrow B.

The second cylindrical hole 17, in the shape of a cylinder, which center is the axis center P1, is provided with the hub 9 at the side of the arrow B of the second taper hole 16 connecting with the second taper hole 16. An end portion 17a at the side of the arrow B of the second cylindrical hole 17 reaches the inside of the main pillar portion 10. The end portion 17a of the second cylindrical hole 17 is in contact with a wall face 10f perpendicular to the directions as shown by the arrows A and B.

On the other hand, a flow hole 19 is provided with the main pillar portion 10 of the hub 9, adjacent to the second cylindrical hole 17 of the needle insertion hole 12 at the side of the arrow B (the right side of the paper of FIG. 2). The flow hole 19 is cylindrically provided such that the center is the axis center P1 and the diameter thereof is smaller than one of the second cylindrical hole 17. The flow hole 19 is provided connecting with the second cylindrical hole 17 of the needle insertion hole 12 such that an opening 19a, in the shape of a circle, is formed at the wall face 10f of the main pillar portion 10 (The needle insertion hole 12 may be formed in any forms in the hub body 90 as long as it is possible to connect with a medium holding space 47 described hereinafter.).

A piston engagement hole 20 is provided with the main pillar portion 10 of the hub 9, adjacent to the flow hole 19 at the side of the arrow B (the right side of the paper of FIG. 2.). The piston engagement hole 20 is comprised of a first taper hole 21, a cylindrical hole 22, a second taper hole 23 and a third taper hole 25.

The first taper hole 21 is provided adjacent to the flow hole 19 at the side of the arrow B (the right side of the paper of FIG. 2) in the main pillar portion 10 of the hub 9. The section of the first taper hole 21 perpendicular to the directions as shown by the arrows A and B is a circular section which center is the axis center P1. The diameter of the section of the first taper hole 21 is made bigger for the direction as shown by the arrow B. The diameter of an end portion 21a, being in the shape of a circular, of the first taper hole 21 at the side of the arrow A is bigger than one of the flow hole 19, that is, the end portion 21a is in contact with a wall face 10g perpendicular to the directions as shown by the arrows A and B. A circular opening 19b is formed at the wall face 10g by the flow hole 19, and the first taper hole 21 and the flow hole 19 communicate with each other through the opening 19b.

The cylindrical hole 22 being in the shape of a cylinder, which ceter is the axis center P1, is provided at the arrow B side of the first taper hole 21, connecting with the first taper hole 21. The second taper hole 23 is provided in the direction as shown by the arrow B at the side of the arrow B of the cylindrical hole 22, contacting with the cylindrical hole 22 such that the diameter of the section perpendicular to the directions as shown by the arrows A and B (that is, the circular section which center is the axis center P1) is made narrower for the direction as shown by the arrow B. The third taper hole 25 is provided in the direction as shown by the arrow B at the side of the arrow B of the second taper hole 23, contacting with the second taper hole 23, and the diameter of the section perpendicular to the directions as shown by the arrows A and B of the third taper hole 25 (the circular section which center is an axis center P2) is made bigger for the direction as shown by the arrow B. Then, a projection 25b is formed such that the part sandwitched between a wall face 23b facing the second taper hole 23 and a wall face 25a facing the third taper hole 25 of the main pillar portion 10 projects for the axis center P1 with a boundary portion 23a between the second taper hole 23 and the third taper hole 25 as an apex.

The arrow B side of the third taper hole 25 is open to the outside such that a circular opening 25c is formed at the end face 10b of the main pillar portion 10 of the hub 9.

The hub insertion portion 4 in a natural state, and the hub 9 are respectively comprised as shown before. The hub insertion portion 4 is elastically deformed as follows and the hub 9 is provided in the hub insertion hole 4b of the hub insertion portion 4 as follows.

Figure 4:
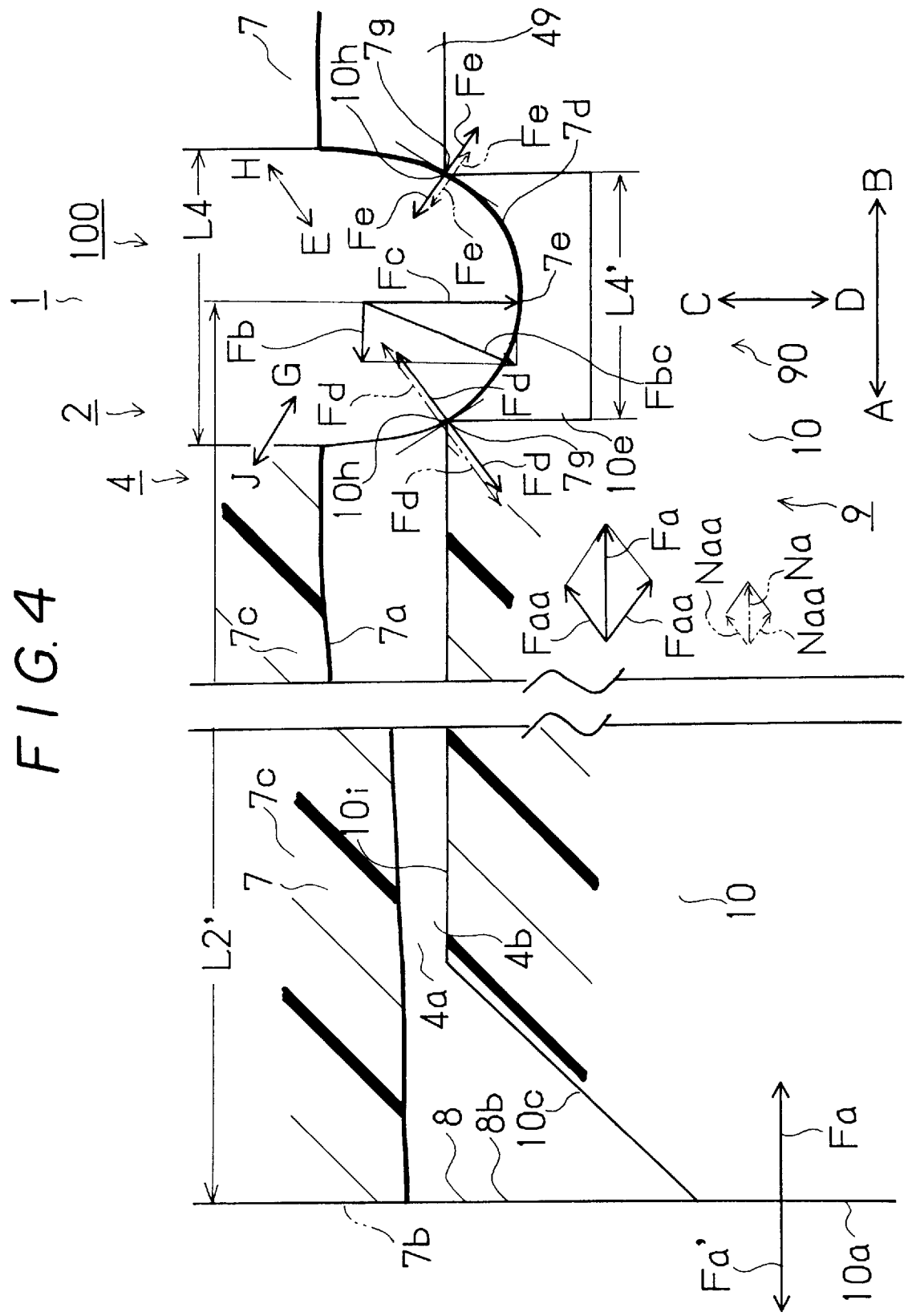
FIG. 4 is a view showing dynamical relation between the hub insertion portion and the hub as shown in FIG. 2.

That is, the hub insertion portion 4, as shown in FIG. 2 or FIG. 4, is elastically deformed in the hub stop rib 7d and near the hub stop rib 7d in the small cylindrical portion 7, expanding in the direction as shown by the arrow C in the figure, that is, for a direction centrifugal with respect to the axis center P1 and extending the extendable portion 7c of the small cylindrical portion 7 in the directions as shown by the arrows A and B (On this occasion, its deformed state is exaggeratedly expressed in the figure for easy understanding.). on the other hand, the hub 9 is provided in such a manner that the main pillar portion 10 of the hub 9 is inserted into the hub insertion space 4a of the hub insertion portion 4 and the small pillar portion 11 of the hub 9 is inserted into the hole 8a of the end wall 8 so as to penetrate the hole 8a. The hub 9 is provided in such a manner that the end face 10a of the main pillar portion 10 of the hub 9 is closely contacted with the wall face 8b at the side of the arrow B of the end wall 8 (the right side of the paper of FIG. 2) (It is not necessary that the end face 10a and wall face 8b are always closely contacted with each other as the present embodiment, and a little gap may be formed therebetween.).

In addition, the hub 9 is provided such that the position of the hub stop rib 7d of the small cylindrical portion 7 and the position of the hub stop groove 10e of the hub 9 are matched in the directions as shown by the arrows A and B. In other words, the extendable portion 7c of the small cylindrical portion 7 extends in the directions as shown by the arrows A and B in such a manner that the distance between the end portion 7b of the small cylindrical portion 7 and the center of the hub stop rib 7d becomes to be the distance L2' (that is, the distance equal to the distance L2' between the end wall 10a in the hub 9 and the center of the hub stop groove 10e) by extending rather than the distance L2 in a natural state.

Furthermore, the hub 9 is provided such that the hub stop rib 7d abuts on the hub 9, and such that the top end 7e side of the hub stop rib 7d is inserted into the hub stop groove 10e which exists at the position corresponding and matching to the hub stop rib 7d in the direction as shown by the arrow D in the figure, that is, in the direction directing to the the axis center P1 (that is, the opposite direction of one as shown by the arrow C). Since the width L4 of the hub stop rib 7d is wider than the width L4' of the hub stop groove 10e, as described before, the hub stop rib 7d abuts on the opening ends 10h, 10h at both sides of the arrows A and B of the hub stop groove 10e in seal portions 7g, 7g at the sides of the arrows A and B of the top end 7e as shown in FIG. 4.

That is, the hub insertion portion 4 expands in such a manner that the inside diameter in the seal portion 7g of the inside diameter of the small cylindrical portion 7 is almost equal to the outside diameter L1' of the hub 9.

The end face 10b of the main pillar portion 10 of the hub 9 is positioned near a boundary between the hub insertion space 4a and the inside space 2a (that is, near a boundary between the inside of the small cylindrical portion 7 and the inside of the taper 6).

The inside diameter excluding the hub stop rib 7d of the small cylindrical portion 7 which expands in the direction as shown by the arrow C is at least bigger than the inside diameter L1 in a natural state, and is bigger than the outside diameter L1' of the main pillar portion 10 of the hub 9. Therefore, the inner peripheral face 7a of the small cylindrical portion 7 is not in contact with the outer peripheral face 10i of the hub 9 in the part excluding the hub stop rib 7d, and a gap space 49 is formed between the inner peripheral face 7a and the outer peripheral face 10i.

Since the hub 9 is made of material harder than the syringe 100, it is hard to elastically deformed, in comparison with the syringe 100. And, the hub 9 is hard to elastically deformed in comparison with the syringe body 2 which is cylindrically formed since the hub 9 is in the shape of a circular cylinder. Therefore, the degree of elastic deformation of the hub 9 is smaller than the syringe 100.

Since the extendable portion 7c of the small cylindrical portion 7 extends in the directions as shown by the arrows A and B by elastic deformation, the extendable portion 7c gives the main pillar portion 10 of the hub 9 a restoring force Fa in the direction as shown by the arrow B from the end face 10a through the end wall 8 unitedly provided with the extendable portion 7c as shown in FIG. 4. Therefore, the main pillar portion 10 of the hub 9 give the end wall 8 a reaction Fa' in the direction as shown by the arrow A against the restoring force Fa in the end face 10a. And, the extendable portion 7c gives the hub stop rib 7d which is unitedly provided with the extendable portion 7c a restoring force Fb in the direction as shown by the arrow A. The restoring force Fa is equal to the restoring force Fb.

Since the hub stop rib 7d and the part near the hub stop rib 7d expand by elastic deformation in the direction as shown by the arrow C, a restoring force Fc in the direction as shown by the arrow D is added to the hub stop rib 7d.

That is, a predetermined restoring force Fbc by the restoring forces Fb, Fc acts on the hub stop rib 7d in the direction for the axis center P1 and in the direction near one as shown by the arrow A, and the portions where the hub 9 and the hub stop rib 7d abut on each other at the sides of the arrow A and the arrow B (that is, each opening end 10h and each seal portion 7g at the sides of the arrow A and arrow B) match with each other by the restoring force Fbc such that seal pressure Fd, Fd and seal pressure Fe, Fe are added, that is, the abutting portions are sealed.

Then, the portion between the wall face 8b of the end wall 8 of the small cylindrical portion 7 and the end face 10a of the hub 9 and the portions between the seal portions 7g, 7g at the sides of the arrows A and B of the hub stop rib 7d and the opening ends 10h, 10h at the sides of the arrows A and B of the hub 9 are sealed, the portions are in a water-tight state (or an airtight state) (If a gap exists between the wall face 8b and the end face 10a of the hub 9, no restoring force Fa, Fb exist, and then only the portion between the hub stop rib 7d and the opening ends 10h, 10h are sealed.).

On this occasion, the restoring forces Fa, Fb, Fc or the restoring force Fbc by these restoring forces Fa, Fb, Fc can be preset in advance as a desired size according to the material of the hub insertion portion 4, the wall thickness of the small cylindrical portion 7 or the position of the hub stop rib 7d and the hub stop groove 10e.

The hub insertion portion 4 is elastically deformed as described before, and the hub 9 is provided with the hub insertion portion 4 as explained hereinbefore.

On the other hand, a needle 26 is inserted into the needle insertion hole 12 of the hub 9, as shown in FIG. 1 or 2. A top end 26a side of the needle 26 is positioned at the outside of the syringe body 2, and the needle 26 is inserted into the needle insertion hole 12 from a rear end portion 26b side. The rear end portion 26b of the needle 26 abuts on the wall face 10f formed at the side of the arrow B of the needle insertion hole 12, and an opening 26d in the rear end 26b of a medium flow hole 26c which penetrates from the top end 26a of the needle 26 to the rear end 26b side is adjusted to the opening 19a of the flow hole 19 formed at the wall face 10f. That is, the medium flow hole 26c and the flow hole 19 communicates with each other through the openings 26d, 19a in the directions as shown by the arrows A and B.

Of the needle insertion hole 12, the space between the needle 26 and the hub 9 is filled with an adhesive 27, and is hardened.

The piston 29 is provided with the syringe assembly 1, as shown in FIG. 1 (FIG. 1 is a typical sectional view of the syringe assembly 1, and with respect to a piston body 30, an outer press plate 32, an inner press plate 33, which are described hereinafter, their sides are shown, not their sections, for convenience.).

The piston 29 has the bar-shaped piston body 30 which extends in the directions as shown by the arrows A and B, the piston body 30 is comprised such that two congruent plate portions 30a, each which is a plate shaped rectangle especially long in the directions as shown by the arrows A and B, are unitedly cross provided with each other such that the sections thereof form the shape of a cross. The width perpendicular to the directions as shown by the arrows A and B of the plate face of the plate portion 30a is almost equal to the inside diameter in the engagement rib 3b of the main cylindrical portion 3, and the piston body 30 is inserted into the main cylindrical portion 3 through the opening end 3a from the arrow A side of the piston body 30.

On each plate portion 30a of the piston body 30, notches 31 are formed from both side portions 30b, 30b of respective plate portions 30a, 30a in the direction of the axis center (that is, the axis center P1) of the piston body in the shape of a wedge near the direction by the arrow A. Four notches 31 are provided at the positions adjusted one another in the directions as shown by the arrows A and B.

The outer press plate 32, which plate face is a circular plate perpendicular to the directions as shown by the arrows A and B, is provided at the end portion side of the arrow B side of the piston body 30, being united with the piston body 30, and coaxial with the piston body 30. The diameter of the outer press plate 32 is fully bigger than the inside diameter of the main cylindrical portion 3.

Figure 5:
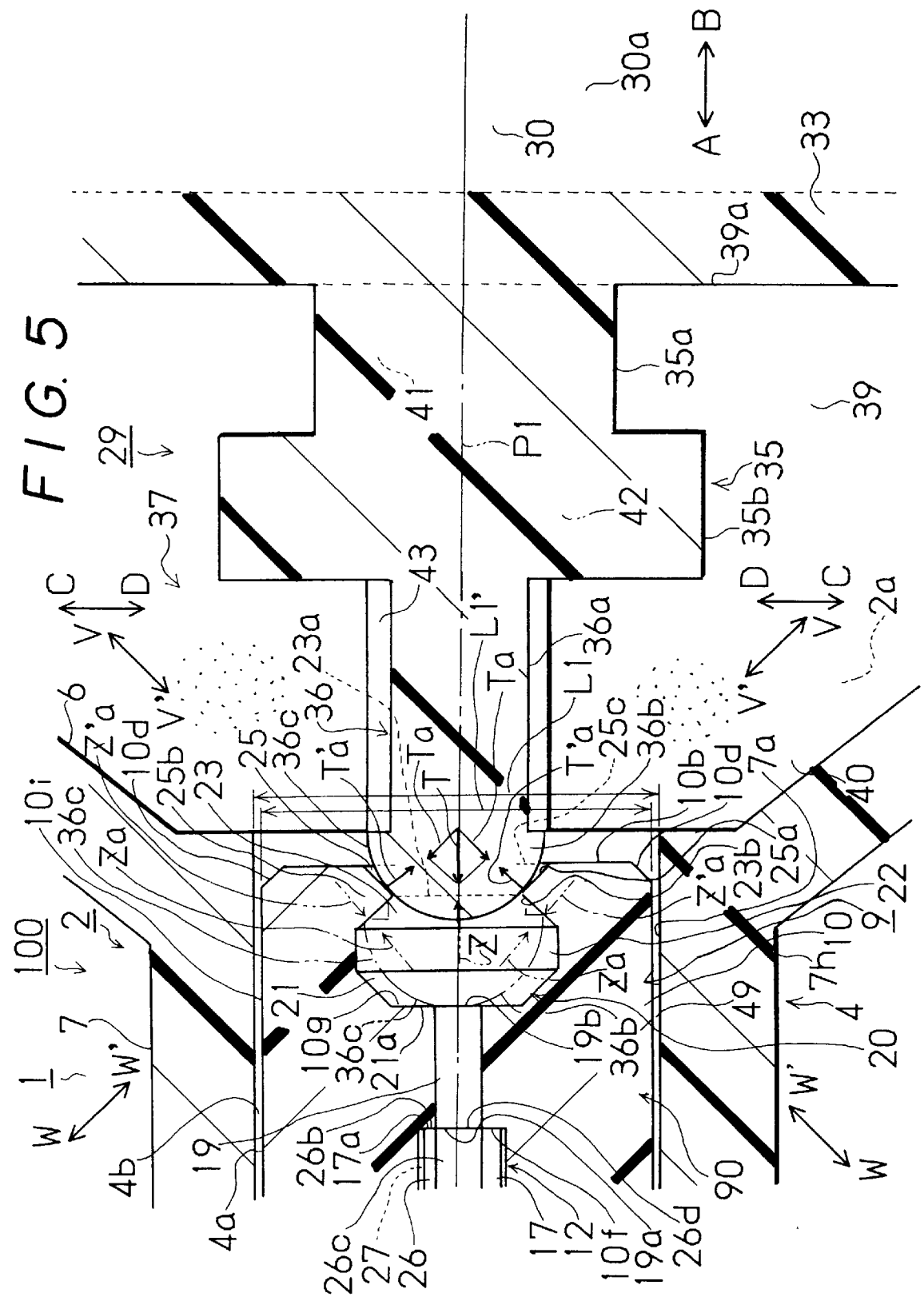
FIG. 5 is a view showing position relation between the hub and a piston as shown in FIG. 1.

As shown in FIG. 1 or 5, the inner press plate 33, which plate face is a circular plate perpendicular to the directions as shown by the arrows A and B, is provided at the end portion side of the arrow A side of the piston body 30 being united with the piston body 30 and coaxial with the piston body 30 (Therefore, the inner press plate 33 is positioned inside the main cylindrical portion 3.). The diameter of the inner press plate 33 is almost equal to the inside diameter of the main cylindrical portion 3 (Therefore, the diameter of the inner press plate 33 is bigger than the inside diameter in the engagement rib 3b of the main cylindrical portion 3.).

As shown in FIG. 1 or 5, a packing support 35 is provided with the inner press plate 33 at the arrow A side. A circular cylindrical portion 35a in the shape of a circular cylinder, which extends in the directions as shown by the arrows A and B, is provided with the packing support 35, coaxial with the inner press plate 33. The diameter of the circular cylindrical portion 35a is smaller than one of the inner press plate 33, and the circular cylindrical portion 35a is provided at the arrow A side of the inner press plate 33, being united with the inner press plate 33. A circular plate portion 35b, which plate face is a circular plate perpendicular to the directions as shown by the arrows A and B, is provided at the arrow A side of the circular cylindrical portion 35a, coaxial with the circular cylindrical portion 35a, united with the circular cylindrical portion 35a. The diameter of the circular plate portion 35b is bigger than one of the circular cylindrical portion 35a, and is smaller than one of the inner press plate 33.

A hub engagement portion 36 is provided at the arrow A side of the circular plate portion 35b, and a circular cylindrical portion 36a in the shape of a circular cylinder, which extends in the directions as shown by the arrows A and B, is provided with the hub engagement portion 36, coaxial with the circular plate portion 35b. The diameter of the circular cylindrical portion 36a is smaller than one of the circular plate portion 35b. The circular cylindrical portion 36a is provided at the arrow A side of the circular plate portion 35b, being united with the circular plate portion 35b. A semi-spherical insertion portion 36b, which diameter is bigger than one of the circular cylindrical portion 36a is provided at the arrow A side of the circular cylindrical portion 36a, united with the circular cylindrical portion 36a, directing a spherical surface 36c to the arrow A side.

The diameter of the circular cylindrical portion 36a is almost equal to the inside diameter of the boundary portion 23a between the second taper hole 23 and the third taper hole 25 of the piston engagement hole 20 provided at the hub 9, and the diameter of the insertion portion 36b is smaller than the inside diameter of the cylindrical hole 22 of the piston engagement hole 20.

On the other hand, a packing 37 made of flexible resin is supportingly provided with the packing support 35. The packing 37 is comprised of a circular cylindrical portion 39, which extends in the directions as shown by the arrows A and B, and a taper 40, connecting the arrow A side of the circular cylindrical portion 39, being united with the circular cylindrical portion 39. The outside diameter of the taper 40 is made narrower for the direction as shown by the arrow A. The form of the taper 40 allow the taper 40 to be inserted into the inside of the taper 6 of the syringe body 2 in a natural state so as to adjust to the inside of the taper 6.

A first hole 41, which diameter is the same as one of the circular cylindrical portion 35a of the packing support 35, and which length in the directions as shown by the arrows A and B is the same as one of the circular cylindrical portion 35a, is provided with the packing 37 in the direction as shown by the arrow A from an end face 39a side of the arrow B side of the circular cylindrical portion 39, coaxial with the circular cylindrical portion 39. Furthermore, a second hole 42, which diameter is the same as one of the circular plate portion 35b of the packing support 35, and which length in the directions as shown by the arrows A and B is the same as one of the circular plate portion 35b, is provided with the packing 37, connecting with the arrow A side of the first hole 41, coaxial with the circular cylindrical portion 39. And, a third hole 43, which diameter is the same as the outside diameter of the section perpendicular to the directions as shown by the arrows A and B of the insertion portion 36b of the hub engagement portion 36, and which length in the directions as shown by the arrows A and B is the same as one of the circular cylindrical portion 36a of the hub engagement portion 36 is provided with the packing 37, connecting with the arrow A side of the second hole 42, coaxial with the circular cylindrical portion 39. The third hole 43 is open at the taper 40 side of the packing 37 in the direction as shown by the arrow A.

In other words, the packing 37 is provided so as to engage with the packing support 35 such that the circular cylindrical portion 36a of the hub engagement portion 36 penetrates the third hole 43, the circular plate portion 35b of the packing support 35 is inserted into the second hole 42, and the circular cylindrical portion 35a of the packing support 35 penetrates the first hole 41.

In such a state that the taper 40 of the packing 37 is inserted into the inside of the taper 6 of the syringe body 2 in a natural state so as to adjust, as shown in FIG. 5, the form of the packing 37 is set in such a manner that the spherical surface 36c of the insertion portion 36b of the hub engagement portion 36 of the arrow A side of the packing support 35 which is engaged with the packing 37 is in contact with the wall face 25a facing the third taper hole 25 of the piston engagement hole 20.

The diameter of the circular cylindrical portion 39 of the packing 37 is almost equal to one of the inner press plate 33. However, at the outer periphery side of the circular cylindrical portion 39 of the packing 37, annular folds 45 are double formed, being arranged in the directions as shown by the arrows A and B along the outer periphery of the circular cylindrical portion 39. Then, the circular cylindrical portion 39 and the fold 45 of the packing 37 are inserted into the main cylindrical portion 3 of the syringe body 2, reducing their sizes by elastic deformation in the direction for the axis center P1 (that is, in the direction as shown by the arrow D.). That is, the circular cylindrical portion 39 of the packing 37 and the fold 45 press the inner peripheral face 3c of the main cylindrical portion 3 with a force in the direction away from the axis center (that is, the direction as shown by the arrow C), and the part between the packing 37 and the main cylindrical portion 3 is sealed with water seal (or air seal). Since the circular cylindrical portion 39 of the packing 37 applys a force so as to reduce the diameter of the first hole 41 and the second hole 42 to the first hole 41 side and the second hole 42 side of the packing 37, the packing support 35 inserted into the first hole 41 and the second hole 42 and the packing 37 closely contact with each other so as to be pressed. The part between the packing 37 and the packing support 35 is sealed with water seal (or air seal).

The inner peripheral face 3c of the main cylindrical portion 3 of the syringe body 2 is smoothly formed, and then, the piston 29, into which the packing 37 is inserted, is slidable in the directions as shown by the arrows A and B in the inside space 2a of the main cylindrical portion 3.

The syringe assembly 1 is comprised as described hereinbefore. In order to assemble the syringe assembly 1, the following steps are executed.

That is, the syringe 100, the hub 9, the needle 26, the piston 29 and the packing 37, which are the comprising parts of the syringe assembly 1, are prepared. At first, the hub 9 is inserted into the syringe 100.

Figure 6:
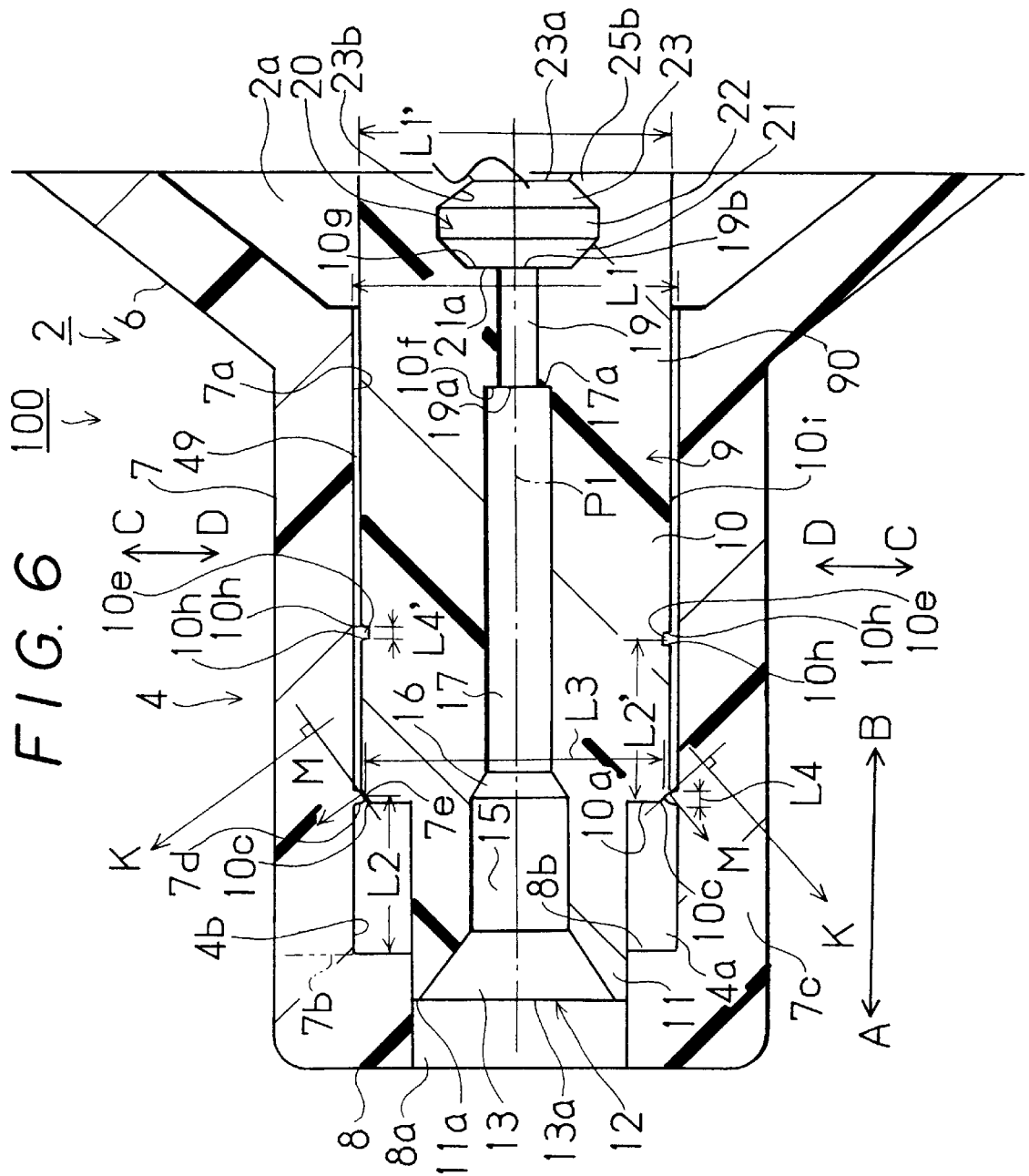
FIG. 6 is a view showing a routine of inserting the hub into the hub insertion portion as shown in FIG. 2.

That is, the hub 9 is inserted into the inside space 2a of the syringe body 2 from the opening end 3a of the syringe body 2. The insertion is executed so as to face the small pillar portion 11 side of the hub 9 to the small cylindrical portion 7 side of the syringe body 2 (the side of the arrow A of the figure). Subsequently, the hub 9 is further inserted into the side of the arrow A of the figure as shown in FIG. 6, and the hub 9 is inserted into the inside of the small cylindrical portion 7 of the syringe body 2, that is, into the hub insertion space 4a to the position at which the chamfer portion 10c of the hub 9 abuts on the hub stop rib 7d having the inside diameter smaller than the outside diameter L1' of the main pillar portion 10 of the hub 9. On this occasion, since the outside diameter L1' of the main pillar portion 10 of the hub 9 and the outside diameter of the small pillar portion 11 (that is, the outside diameter smaller than the outside diameter L1') are smaller than the inside diameter L1 of the part in which the hub stop rib 7d is not formed of the small cylindrical portion 7, the hub 9 is smoothly inserted into the hub insertion space 4a of the small cylindrical portion 7 to the position at which the chamfer portion 10c of the hub 9 abuts on the hub stop rib 7d having the inside diameter L3 smaller than the inside diameter L1'.

While the hub 9 is inserted to the position at which the chamfer portion 10c of the hub 9 abuts on the hub stop rib 7d, the end face 1 ha of the arrow A side of the small pillar portion 11 of the hub 9 reaches the position of the wall face 8b of the arrow B side of the end wall 8 of the hub insertion portion 4. However, since the hole 8a of the end wall 8 is at the position corresponding to the small pillar portion 11 in the directions as shown by the arrows C and D, and its diameter is bigger than one of the small pillar portion 11, the end face h1a reaches the hole 8a so as to adjust when the end face 11a of the small pillar portion 11 reaches the wall face 8b of the end wall 8. That is, the hub 9 is inserted to the position at which the chamfer portion 10c of the hub 9 abuts on the hub stop rib 7d, thereby the small pillar portion 11 is smoothly inserted into the hole 8a of the end wall 8.

After the chamfer portion 10c abuts on the hub stop rib 7d, as shown in FIG. 6, a force in the direction as shown by the arrow A is added to the hub 9 from the end portion 10b side of the arrow B side of the hub 9. The force in the direction as shown by the arrow A is added to the hub 9, thereby the hub 9 gives an action force M to the hub stop rib 7d at the position at which the chamfer portion 10c abuts on the hub stop rib 7d in the direction perpendicular to the tapered surface of the chamfer portion 10c, that is, in the direction as shown by the arrow K in the figure.

Of the action force M, the component force of a component of the direction as shown by the arrow A is balanced in the hub stop rib 7d and the like as shearing stress or bending stress. Of the action force M, the component force of the component in the direction as shown by the arrow C presses the small cylindrical portion 7 through the hub stop rib 7d in the direction as shown by the arrow C. The small cylindrical portion 7 is easy to elastically deformed against the force in the direction as shown by the arrow C for its construction, and therefore, the small cylindrical portion 7 expands at the hub stop rib 7d and near the hub stop rib 7d in the direction as shown by the arrow C by the component force of the component in the direction as shown by the arrow C of the action force M.

Since the hub stop rib 7d of the small cylindrical portion 7 and the portion near the hub stop rib 7d expand in the direction as shown by the arrow C, the inside diameter in the hub stop rib 7d of the small cylindrical portion 7 is broadened, and the hub 9 receiving the force pressing in the direction as shown by the arrow A advances in the direction as shown by the arrow A as the inside diameter is broadened.

At the position at which the hub 9 advances in the direction as shown by the arrow A, the hub 9 further presses the hub stop rib 7d in the chamfer portion 10c, and the hub stop rib 7d of the small cylindrical portion 7 and the part near the hub stop rib 7d further expand in the direction as shown by the arrow C by the component force of the component in the direction as shown by the arrow C of the force pressing the hub stop rib 7d. The inside diameter in the hub stop rib 7d of the small cylindrical portion 7 is further broadened, the hub 9 receiving the force pressing in the direction as shown by the arrow A further advances in the direction as shown by the arrow A as the inside diameter is broadened. Furthermore, the hub 9 is advanced in the direction as shown by the arrow A while the force in the direction as shown by the arrow A is added to the hub 9 and the hub stop rib 7d and the part near the hub stop rib 7d are further expanded in the direction as shown by the arrow C. Then, the hub 9 is advanced to the position at which the hub stop rib 7d abuts on the hub 9 at the nearest side to the arrow B of the chamfer portion 10c, that is, in the outer peripheral face 10i of the main pillar portion 10.

Figure 7:
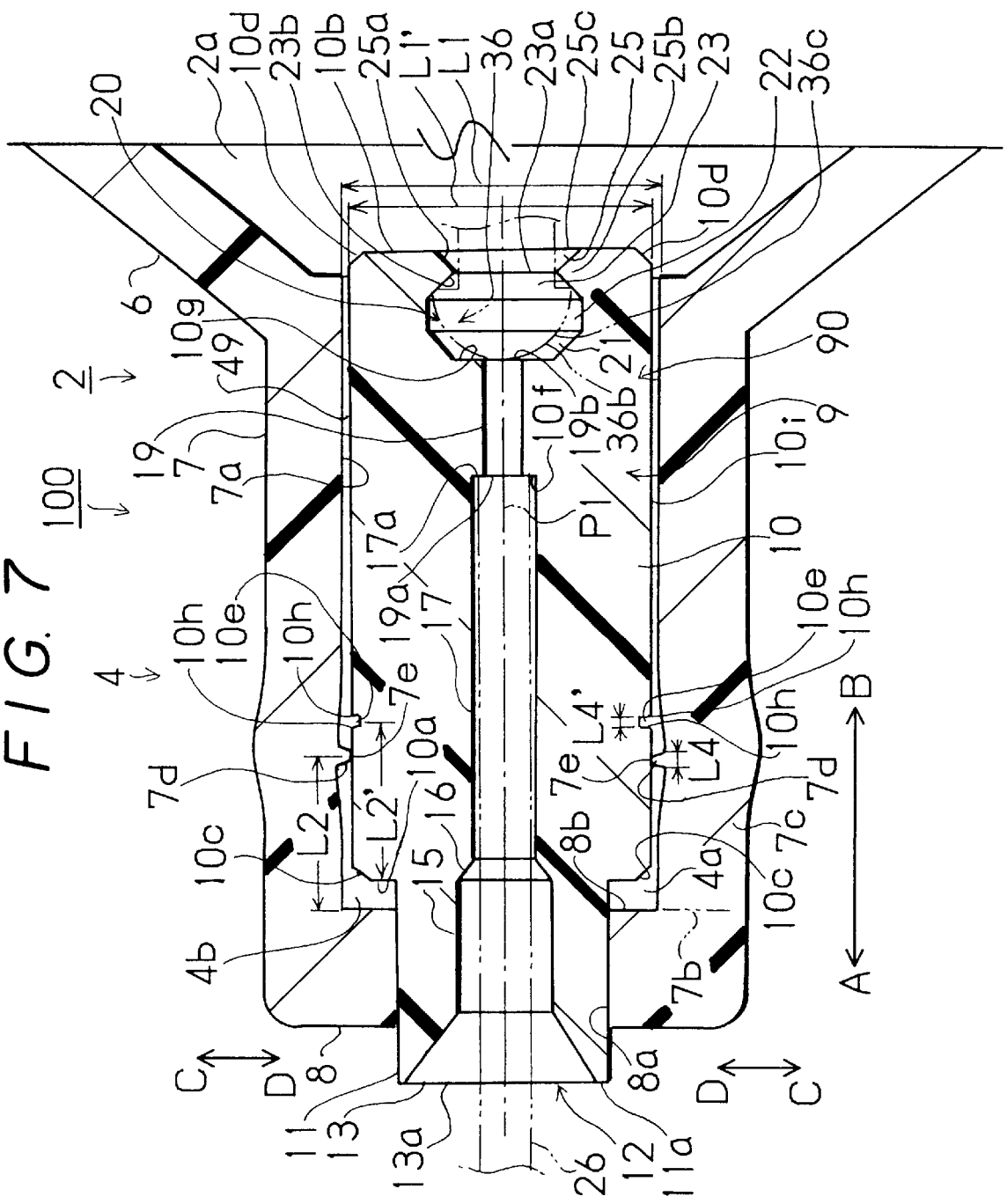
FIG. 7 is a view showing a routine of inserting the hub into the hub insertion portion as shown in FIG. 2.

The hub 9 advances to the position at which the hub stop rib 7d abuts on the outer peripheral face 10i of the main pillar portion 10, thereby the restoring force restoring the hub stop rib 7d and the portion near the hub stop rib 7d in the direction as shown by the arrow D is added to the main pillar portion 10 in the outer peripheral face 10i through the hub stop rib 7d at the portion abutting the hub stop rib 7d and the outer peripheral face 10i on each other, as shown in FIG. 7. Therefore, when the hub 9 is further advanced in the direction as shown by the arrow A adding a force in the direction as shown by the arrow A at the position at which the hub stop rib 7d abuts on the outer peripheral face 10i of the main pillar portion 10, a frictional force acts on the hub 9 in the direction as shown by the arrow B by the force acting on the hub 9 in the outer peripheral face 10i in the direction as shown by the arrow D. That is, the hub 9 is further advanced in the direction as shown by the arrow A adding a force in the direction as shown by the arrow A being capable of resisting the frictional force. The hub 9 is further advanced in the direction as shown by the arrow A until the end face 10a of the main pillar portion 10 of the hub 9 is closely contacted with the wall face 8b of the arrow B side of the end wall 8.

After the hub 9 is advanced till close contact, furthermore, the hub 9 is pressed in the direction as shown by the arrow A. By the press the hub 9 gives the end wall 8 closely contacting with the arrow A side of the hub 9 a force in a direction as shown by the arrow A, and the force is transferred to the extendable portion 7c of the small cylindrical portion 7 being unitedly provided with the end wall 8 (and each portion of the remaining syringe body 2). Therefore, the extendable portion 7c extends in its length in the directions as shown by the arrows A and B by elastic deformation. Furthermore, the press is continued so as to extend the extendable portion 7c, and the press is continued till the distance between the wall face 8b of the end wall 8 and the hub stop rib 7d in the directions as shown by the arrows A and B becomes to be the distance L2' from the distance L2.

With the extending of the extendable portion 7c, the hub stop rib 7d moves relative to the hub 9 at the arrow B side along the outer peripheral face 10i of the hub 9 and the distance between the wall face 8a of the end wall 8 and the hub stop rib 7d becomes to be the distance L2', thereby the position of the hub stop rib 7d and the position of the hub stop groove 10e of the hub 9 are adjusted to each other. Since a restoring force in the direction as shown by the arrow D is acted on the hub stop rib 7d and the portion near the hub stop rib 7d, the position of the hub stop rib 7d and the position of the hub stop groove 10e are adjusted to each other, thereby the hub stop rib 7d and the portion near the hub stop rib 7d slightly restore in the direction as shown by the arrow D, inserting the top end 7e side of the hub stop rib 7d into the hub stop groove 10e in the direction as shown by the arrow D (In this case, both can not restore to their natural state.). And, the top end 7e side of the hub stop rib 7d is inserted into the hub stop groove 10e in the direction as shown by the arrow D, thereby the hub stop rib 7d is engaged with the hub 9, abutting on the opening ends 10h, 10h of both A and B sides of the hub stop groove 10e. The portions abutting on the opening ends 10h, 10h of the hub stop rib 7d are the seal portions 7g, 7g, as decribed before.

Then, the insertion of the hub 9 into the syringe 100 finishes. As described before, the hub 9 is fixed by the small cylindrical portion 7 balancing respective forces between the hub 9 and the small cylindrical portion 7, as described hereinbefore.

The insertion operation of the hub 9 into the syringe 100 is executed by pressing the hub 9 so as to insert, and then, it is easy without complex assembling operations.

Subsequently, the packing 37 is inserted into the piston 29. In the first place, the first hole 41 of the packing 37 is broadened with hands or the like so as to equalize the diameter of the first hole 41 with one of the circular plate portion 35b of the packing support 35, making use of the flexibility of the packing 37. After that, the hub engagement portion 36 side of the piston 29 is inserted in the direction as shown by the arrow A from the first hole 41 side of the packing 37. Next, the piston 29 is further inserted until the insertion portion 36b of the hub engagement portion 36 passes and penetrates the third hole 43 of the packing 37 in the direction as shown by the arrow A and the insertion portion 36b projects at the side of the arrow A of the taper 40 of the packing 37, that is, the circular cylindrical portion 36a of the hub engagement portion 36 is inserted into the third hole 43 and the circular cylindrical portion 35a of the packing support 35 and the circular plate portion 35b are inserted into the first hole 41 and the second hole 42 which are respectively broadened.

After that, the hand by which the first hole 41 is broadened is left therefrom so as to return the packing 37 to its natural state, thereby the insertion of the packing 37 is finished.

Subsequently, the piston 37, into which the packing 37 is inserted, is inserted into the syringe body 2.

The insertion of the piston 29 is executed in such a manner that the side, at which the packing 37 of the piston 29 is inserted, is inserted into the inside space 2a of the syringe body 2 from the opening end 3a side of the syringe body 2.

On this occasion, the outside diameter in the fold 45 of the circular cylindrical portion 39 of the packing 37 in a natural state is bigger than the inside diameter of the main cylindrical portion 3 of the syringe body 2. However, the packing 37 can be inserted into the inside space 2a of the syringe body 2 by reducing the outside diameter of the fold 45 of the packing 37 making use of the flexibility of the packing 37.

That is, the taper 40 side of the packing 37 is adjusted to the opening end 3a, and after that, the piston 29 is pressed in the direction as shown by the arrow A, thereby the packing 37 is inserted into the inside space 2a of the syringe body 2, adjusting to the inside space 2a of the syringe body 2, that is, reducing the outside diameter of the fold 45 of the circular cylindrical portion 39 of the packing 37.

Since the outside diameter of the inner press plate 33 and the width of the plate portion 30a of the piston body 30 are almost equal to the inside diameter of the main cylindrical portion 3 of the syringe body 2 (or smaller), the inner press plate 33 and the piston body 30 are smoothly inserted into the inside space 2a of the syringe body 2.

By inserting the piston 2 into the direction as shown by the arrow A, the packing 37 and the inner press plate 33 pass the position of the engagement rib 3b of the main cylindrical portion 3.

When the packing 37 passes the position of the engagement rib 3b, the packing 37 receives the reaction against the force pressing the piston 29 in the direction as shown by the arrow A from the engagement rib 3b, and passes reducing the outside diameter of the circular cylindrical portion 39 and the fold 45 so as to equalize with the inside diameter of the engagement rib 3b of the main cylindrical portion 3 of the syringe body 2 by the reaction.

When the inner press plate 33 passes the position of the engagement rib 3b continuing the packing 37, the periphery side of the inner press plate 33, which outside diameter is bigger than the inside diameter of the engagement rib 3b, abuts on the engagement rib 3b. In case of abutting, the force pressing the piston 29 in the direction as shown by the arrow A elastically expands the portion near the engagement rib 3b of the main cylindrical portion 3 in the direction as shown by the arrow C through the inner press plate 33, and through the engagement rib 3b abutting on the inner press plate 33. Therefore, the inner press plate 33 passes the position of the engagement rib 3b, broadening the inside diameter in the engagement rib 3b. After the passing, the inner press plate 33 leaves from the engagement rib 3b, and then, no force expanding the main cylindrical portion 3 in the direction as shown by the arrow C acts, and the portion near engagement rib 3b of the main cylindrical portion 3 restores in the direction as shown by the arrow D.

After the packing 37 and the inner press plate 33 pass the position of the engagement rib 3b of the main cylindrical portion 3, the piston 29 is further inserted in the direction as shown by the arrow A, and the piston 29 is inserted to the position, at which the taper 40 of the packing 37 is inserted into the inside of the taper 6 of the syringe body 2 so as to adjust, and then, the insertion of the piston 29 finishes.

In such a state that the taper 40 of the packing 37 is inserted into the inside of the taper 6 of the syringe body 2 so as to adjust, as described hereinbefore, the insertion portion 36b of the hub engagement portion 36 of the piston 29 exists in such a manner that the spherical surface 36c side of the insertion portion 36b is in contact with the wall face 25a facing the third taper hole 25 of the piston engagement hole 20, which is provided with the hub 9.

Subsequently, the needle 26 is inserted into the needle insertion hole 12 of the hub 9 so as to attach. That is, the needle 26 is inserted from the rear end 26b side of the needle 26 into the needle insertion hole 12 in the direction as shown by the arrow B, as shown in FIG. 2 till the rear end 26b abuts on the wall face 10f of the hub 9 of the bottom of the needle insertion hole 12. After the insertion, the space between the hub 9 in the needle insertion hole 12 and the needle 26 is filled with the adhesive 27, and then, the adhesive 27 is hardened. Then, insertion of the needle 26 in the hub 9 finishes.

When the needle insertion hole 12 is filled with the adhesive 27, the adhesive 27 can flow to the bottom side of the needle insertion hole 12 (that is, the arrow B side) without forming a space in the needle insertion hole 12 to the utmost by the first taper hole 13 and the second taper hole 16 which are provided with the needle insertion hole 12.

Assembly of the syringe assembly 1 finishes by the end of insertion of the needle 26.

As described hereinbefore, most operations in assembly of the syringe assembly 1 (that is, all operations excluding one for insertion of the needle 26) are executed by pressing, and therefore, the assembly of the syringe assembly 1 is easy without complex operations.

The syringe assembly 1 assembled as shown below, is used and, after that, the syringe assembly 1 is discarded as follows.

At first, the syringe assembly 1 assembled is filled with a liquid injection medium 46. Filling of the injection medium 46 is executed in such a manner that the main cylindrical portion 3 of the syringe body 2 of the syringe assembly 1 is grasped and supported with one hand, and the top end 26a of the needle 26 of the syringe assembly 1 is inserted into the injection medium 46 which is inside of a medicine bottle (not shown), and after that, the piston 29 is pulled out to the syringe body 2 in the direction as shown by the arrow B being grasped the outer press plate 32 of the piston 29 with the other hand. Of the inside space 2a of the syringe body 2, the space at the side of the arrow A rather than the packing 37 or the hub engagement portion 36, that is, the medium holding space 47 communicates with the outside of the top end 26a side of the needle 26, that is, inside of a medicine bottle (not shown) through the medium flow hole 26c of the needle 26, the flow hole 19 and the piston engagement hole 20 of the hub 9 in the directions as shown by the arrows A and B. And, the medium holding space 47 is broadened by pulling the piston 29 to the syringe body 2 in the direction as shown by the arrow B, and then, the pressure of the air of the medium holding space 47 (or the injection medium 46) is lowered. Therefore, a differencial pressure arises between the medium holding space 47 and the outside of the top end 26a side of the needle 26, that is, inside of the medicine bottle (not shown), and the injection medium 46 in the medicine bottle flows in the medium holding space 47 through the medium flow hole 26c of the needle 26, and the flow hole 19 and the piston engagement hole 20 of the hub 9.

Filling of the injection medium 46 finishes in such a manner that the piston 29 is further pulled to the syringe body 2 in the direction as shown by the arrow B so as to further broaden the medium holding space 47 and so as to stream a predetermined amount of the injection medium 46 into the medium holding space 47 (The medium holding space 47 may be filled with the injection medium 46, which amount is slightly more than a predetermined amount, and after that, the air or surplus injection medium 46 and the like in the medium holding space 47 may be expelled to the outside through the needle 26 and the like by pressing the piston 29 to the syringe body 2 in the direction as shown by the arrow A with the syringe assembly 1 supported directing to the upper.).

On this occasion, differencial pressure arises between the medium holding space 47 and the outside of the medium holding space 47 at the time of filling of the injection medium 46, and therefore, a differencial pressure force Na acts on the hub 9, which separates the medium holding space 47 from the outside of the medium holding space 47 in the direction as shown by the arrow B, as shown by two-dot chain line of FIG. 4

A predetermined restoring force Fbc is set so as not to respectively disengage the seal portions 7g, 7g of both sides of the arrows A and B from the opening ends 10h, 10h so that both seal pressure Fd and Fe, as shown by the two-dot chain line in FIG. 4, which respectively act between the seal portions 7g, 7g and the opening ends 10h, 10h at both sides of the arrows A and B, may not become to be zero or minus if the most differencial pressure force Na potential acts.

Then, the injection medium 46 in the medium holding space 47 flows in the hub insertion space 4a of the hub insertion portion 4, and furthermore, to the gap space 49 between the hub 9 and the small cylindrical portion 7 from the hub insertion space 4a. However, since the portion between the seal portion 7g of the arrow B side of the hub stop rib 7d and the opening end 10h of the arrow B side of the hub 9 is sealed, the injection medium 46 passes between the seal portion 7g of the arrow B side and the opening end 10h and does not leak in the arrow A side and the like of the hub stop rib 7d. In addition, since not only one portion between the seal portion 7g of the arrow B side and the opening end 10h, the portion between the seal portion 7g of the arrow A side and the opening end 10h, and the portion between the end wall 8 and the end face 10a of the hub 9 are also sealed, thereby safety with respect to leak of the injection medium 46 is extremely improved.

Since the seal between the hub stop rib 7d and the hub 9 is a position contact between the seal portions 7g, 7g and the opening ends 10h, 10h, the seal pressure is equally acted on each sealed portion, and therefore, its credibility is high.

On the other hand, in the packing 37, as described below, the circular cylindrical portion 39 and the fold 45 of the packing 37 are inserted into the main cylindrical portion 3 of the syringe body 2 reducing in the direction as shown by the arrow D by elastic deformation. That is, the circular cylindrical portion 39 of the packing 37 and the fold 45 press the inner peripheral face 3c of the main cylindrical portion 3 with a force in the direction as shown by the arrow C, and the portion between the packing 37 and the main cylindrical portion 3 is sealed with water seal (air seal). That is, the injection medium 46 of the medium holding space 47 does not leak in the inside space 2a of the arrow B side of the packing 37 and the like, passing between the packing 37 and the main cylindrical portion 3.

In addition, since the circular cylindrical portion 39 of the packing 37 and the fold 45 are reduced in the direction as shown by the arrow D by elastic deformation, the packing support 35 of the piston 29, which is inserted into the first hole 42 and the second hole 43 of the packing 37, is pressed by the packing 37 in the direction as shown by the arrow D. That is, the portion between the packing 37 and the packing support 35 is closely sealed. Therefore, the injection medium 46 of the medium holding space 47 can flow to the third hole 43 of the packing 37, but the injection medium 46 does not leak in the inside space 2a of the arrow B side of the packing 37 and the like, further passing between the packing 37 and the packing support 35 in the second hole 42 and the first hole 41.

After filling of the injection medium 46, the needle 26 of the syringe assembly 1 is stuck in a patient's arm with the main cylindrical portion 3 of the syringe assembly 1 supported with one hand.

Subsequently, the main cylindrical portion 3 of the syringe body 2 of the syringe assembly 1 is grasped with fingers of one hand, and the syringe support 5 is supported and fixed in the direction as shown by the arrow B from a plate face of the arrow A side of the syringe support 5 with the fingers which grasp the main cylindrical portion 3. The outer press plate 32 of the piston 29 is pressed in the direction as shown by the arrow A with other finger (the thumb) of the same hand as one of the fingers, by which the main cylindrical portion 3 is grasped so as to drive the piston 29 to the syringe body 2 in the direction as shown by the arrow A. By drive of the piston 29, the capacity of the medium holding space 47 reduces, thereby the injection medium 46 in the medium holding space 47 is pressurized. By pressure, pressure difference arises between the medium holding space 47 and the outside of the top end 26a side of the needle 26, that is, the body of a patient. Therefore, the injection medium 46 of the medium holding space 47 flows in the body in the injection part of a patient through the piston engagement hole 20 of the hub 9, the flow hole 19 and the medium flow hole 26c of the needle 26.

Figure 8:
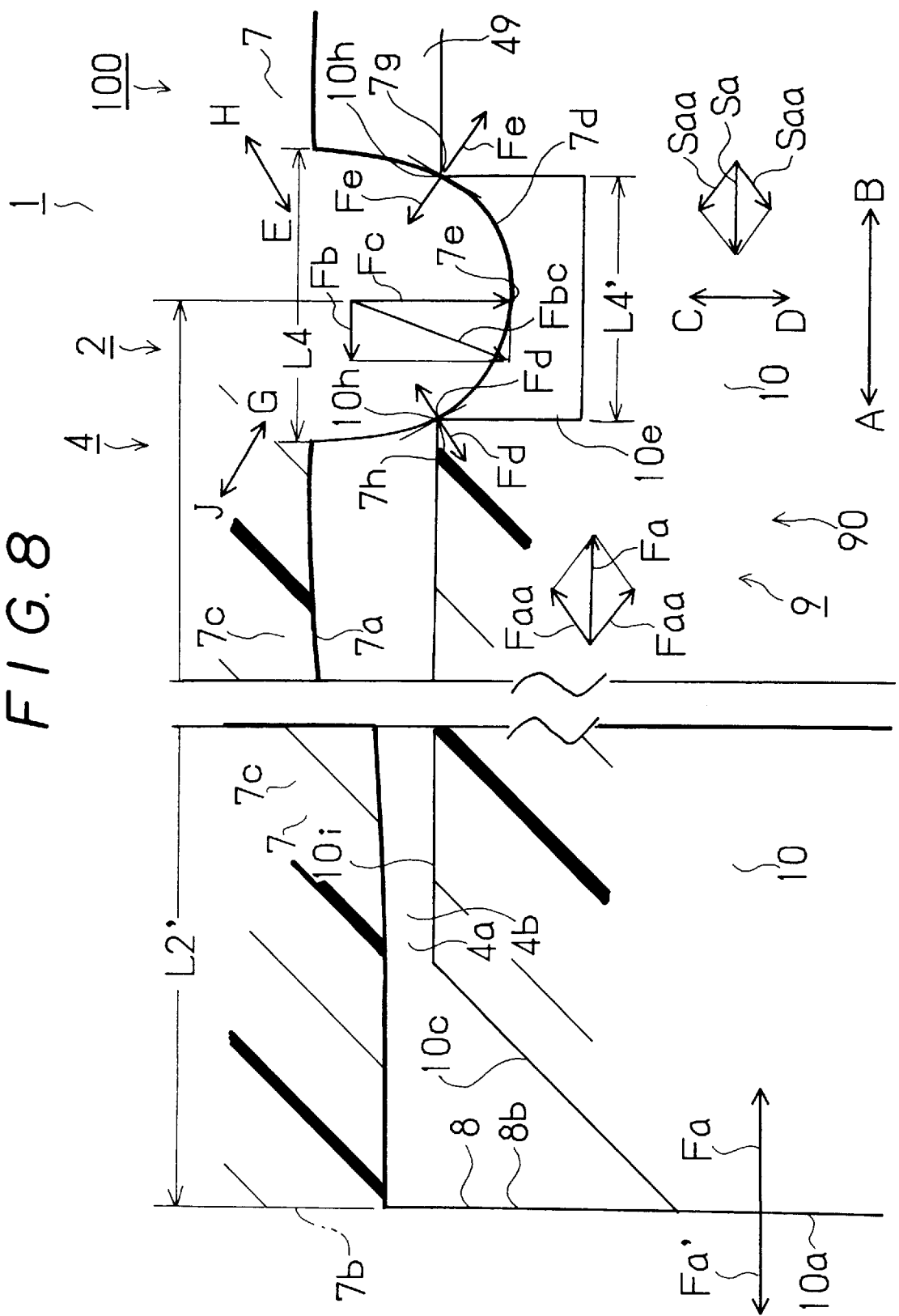
FIG. 8 is a view showing dynamical relation between the hub insertion portion and the hub as shown in FIG. 2.
Figure 9:
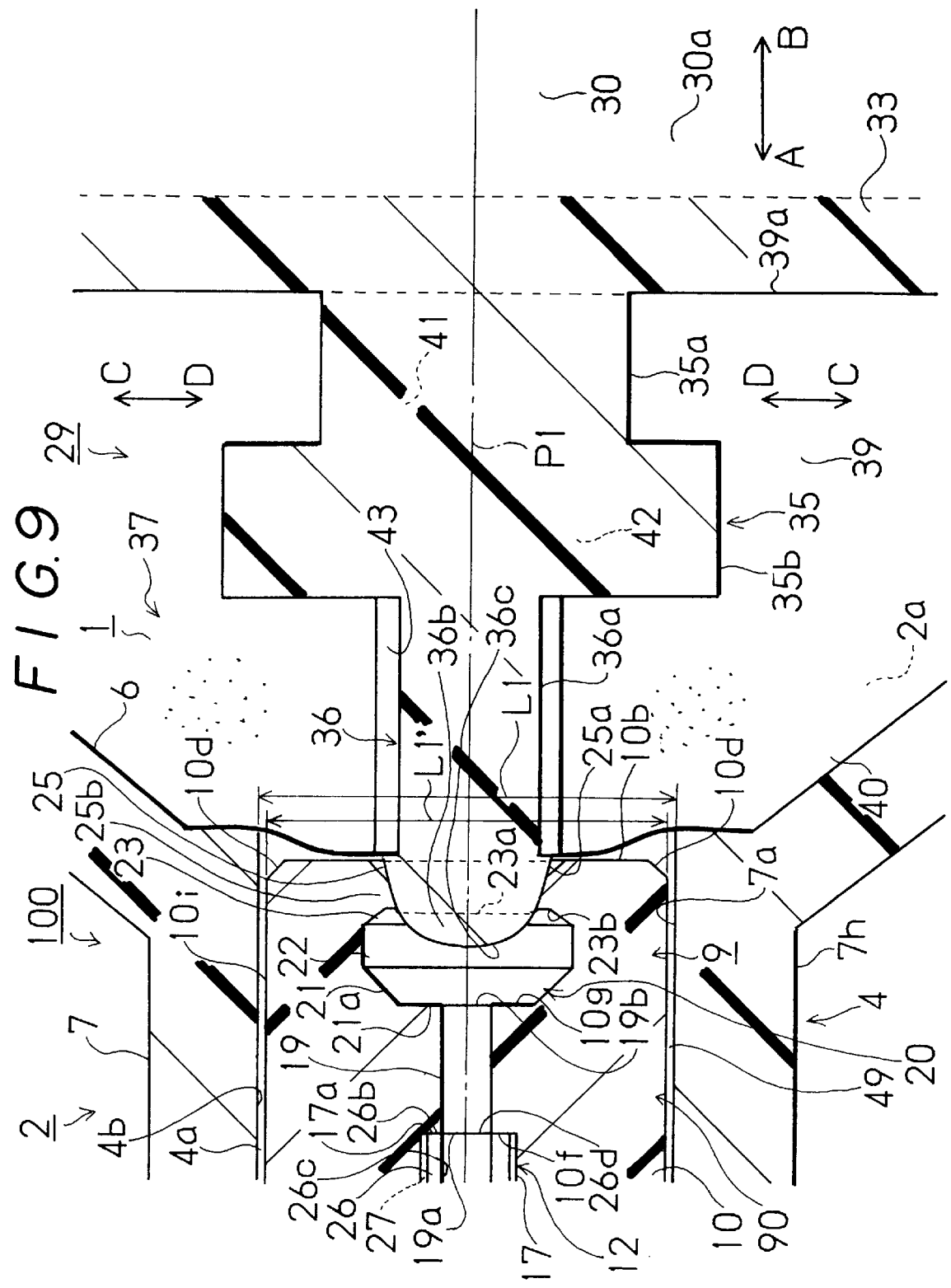
FIG. 9 is a view showing a routine of engaging the hub as shown in FIG. 2 with the piston.

As described before, the injection medium 46 in the medium holding space 47 is pressurized and an action force Sa by the pressure of the injection medium 46 is acted on the hub 9 in the direction as shown by the arrow A from the end face 10b side of the hub 9 adjacent to the injection medium 46, as shown in FIG. 8.

A predetermined restoring force Fbc is set so as not to respectively disengage the seal portions 7g, 7g at both sides of the arrows A and B from the opening ends 10h, 10h so that both seal pressure Fd and Fe, which respectively act between the seal portions 7g, 7g and the opening ends 10h, 10h at both sides of the arrows A and B, may not become to be zero or minus if the most action force Sa potential acts.

Therefore, the portion between the end wall 8 and end face 10a of the hub 9 and the portion between the seal portions 7g, 7g of both sides of the arrows A and B of the hub stop rib 7d and the opening ends 10h, 10h of both sides of the arrows A and B of the hub 9 are continuously sealed and water tight state (or air tight state) is maintained.

After the predetermined amount of the injection medium 46 is streamed in the body of a patient, that is, after the taper 40 of the packing 37 is inserted in the inside of the taper 6 of the syringe body 2 so as to adjust, and the piston 29 is driven until the insertion portion 36b of the hub engagement portion 36 of the piston 29 abuts on the third taper hole 25 of the piston engagement hole 20 of the hub 9, as shown in FIG. 5, the whole syringe assembly 1 is pulled in the direction as shown by the arrow B with respect to a patient through the hand or fingers supporting the syringe assembly 1 therewith so as to pull out the needle 26 from the injection part of a patient.

After pulling the needle 26, the piston 29 and the hub 9 are engaged with each other.

That is, the outer press plate 32 of the piston 29 is further pressed with a finger in the direction as shown by the arrow A.

Just after finish of the flow operation of the injection medium 46 into a body, the taper 40 of the packing 37 is inserted in the inside of the taper 6 of the syringe body 2 so as to adjust, the insertion portion 36b is inserted into the inside of the third taper hole 25 so as to adjust. Therefore, a force in the direction as shown by the arrow A acts on the packing 37 as the insertion portion 36b is advanced in the third taper hole 25 in the direction as shown by the arrow A by driving the piston 29. Since the packing 37 is supported by the taper 6 in the direction as shown by the arrow B, it can not move in the direction as shown by the arrow A. However, the packing 37 has flexibility, and the only insertion portion 36b moves in the direction as shown by the arrow A, and the packing 37 itself remains reducing in the directions as shown by the arrows A and B by elastic deformation.

Since a force in the direction as shown by the arrow A is added to the piston 29 by pressing pressure, a pressing force T in the direction as shown by the arrow A is added to the insertion portion 36b of the hub engagement portion 36, as shown in FIG. 5.

The pressing force T acts to the hub 9 from the insertion portion 36b at the portion, at which the insertion portion 36b and the wall face 25a abut on each other, as a component force Ta in the direction, in which the insertion portion 36b and the wall face 25a of hub 9 facing the third taper hole 25 abut on each other, that is, in the direction as shown by the arrow W in the figure perpendicular to the wall face 25a (that is, the direction away from the axis center P1 and in the direction near the direction as shown by the arrow A). In addition, a reaction Ta' of the component force Ta acts to the insertion portion 36b from the hub 9 at the portion, where the insertion portion 36b abuts on the wall face 25a, in the direction as shown by the arrow W', which is opposite of the direction as shown by the arrow W.

By the component Ta, the projection 25b of the hub 9 which abuts on the insertion portion 36b in the wall face 25a, is elastically deformed in the direction as shown by the arrow W enlarging the diameter of the projection 25b in an apex, that is, the diameter in the boundary portion 23a. In addition, by the reaction Ta', the insertion portion 36b is elastically deformed reducing the diameter of the section perpendicular to the axis center P1.

The piston 29 is further pressed in the direction as shown by the arrow A so as to further advance the insertion portion 36b in the third taper hole 25 in the direction as shown by the arrow A. That is, the insertion portion 36b passes the boundary portion 23a in the direction as shown by the arrow A, reducing the diameter of the insertion portion 36b and enlarging the diameter of the boundary portion 23a so as to correspond the diameter of the insertion portion 36b with one of the boundary portion 23a. After the whole insertion portion 36b completely passes the boundary portion 23a, the press of the piston 29 finishes.

The whole insertion portion 36b completely passes the boundary portion 23a, thereby the insertion portion 36b is inserted in the space formed by the first taper hole 21, the cylindrical hole 22 and the second taper hole 23 as shown by the two-dot chain line of FIG. 5 so as to adjust. The circular cylindrical portion 36a extending at the arrow B side of the insertion portion 36b exists penetrating the boundary portion 23a in the directions as shown by the arrows A and B. Then, the pistion 29 and the hub 9 engage with each other.

The pressing force T in the direction a s shown by the arrow A acts on the insertion portion 36b, thereby the pressing force T in the direction as shown by the arrow A acts on the hub 9 also (This is because the resultant force of the component force Ta of the pressing force T is the pressing force T.). However, the hub 9 is supported in the direction as shown by the arrow B with a hand supporting the syringe body 2 through the hub stop rib 7d of the hub insertion portion 4 or the wall face 8b of the end wall 8 formed meeting at right angles with respect to the axis center P1, and therefore, it receives reaction against the pressing force T in the direction as shown by the arrow B from the hub stop rib 7d or end wall 8. That is, the hub 9 is not almost moved in the direction as shown by the arrow A and the like if the pressing force is received, and the hub 9 is not pulled out of the hole 8a of the end wall 8 in the direction as shown by the arrow A.

After the piston 29 and the hub 9 are engaged with each other, the main cylindrical portion 3 of the syringe body 2 is supported with one hand, the outer press plate 32 is pulled to the syringe body 2 in the direction as shown by the arrow B with the other hand. By pulling the outer press plate 32, the action force Z in the direction as shown by the arrow B acts on the piston 29 and the insertion portion 36b of the hub engagement portion 36, as shown by the two-dot chain line in FIG. 5.

The action force Z acts to the hub 9 from the insertion portion 36b at the portion, at which the insertion portion 36b and the wall face 23b abut on each other, as a component force Za in the direction, in which the insertion portion 36b and the wall face 23b of hub 9 facing the second taper hole 23 abut on each other, that is, in the direction as shown by the arrow V in the figure perpendicular to the wall face 23b (that is, the direction away from the axis center P1 and in the direction near the direction as shown by the arrow B). In addition, the reaction Za' of the component force Za acts to the insertion portion 36b from the hub 9 at the portion, where the insertion portion 36b abuts on the wall face 23b, in the direction as shown by the arrow V', which is opposite of the direction as shown by the arrow V.

As described heretofore, the reaction Za' becomes to be a force reducing the insertion portion 36b in the direction as shown by the arrow V'. However, the reaction Za' is smaller than the force relatively reducing the insertion portion 36b till the insertion portion 36b passes the diameter of the boundary portion 23a.

In addition, the action force Z in the direction as shown by the arrow B acts on the insertion portion 36b, thereby the action force Z in the direction as shown by the arrow B acts on the hub 9 also (This is because the resultant force of the component force Za of the action force Z is the action force Z.). Even in case where the hub 9 is moved to the syringe body 2 in the direction as shown by the arrow A and then the hub 9 is disengaged from the hub stop rib 7d when the piston 29 is engaged with the hub 9, the hub 9 moves to the syringe body 2 in the direction as shown by the arrow B by the action force Z, thereby the hub 9 and the hub stop rib 7d are once returned to the position similar to the position where both are engaged with each other again. Dynamical relation between the hub insertion portion 4 and the hub 9 when the action force Z acts is not illustrated. However, the action force Z acts in the same direction as one of the differential pressure force Na. And, the action force Z acts in the same direction as one of the differential pressure force Na generating at the time of filling of the injection medium 46, but the action force Z is bigger than the most differential pressure force Na potential.

On this occasion, a predetermined restoring force Fbc is set so as to sufficiently emulate the most differential pressure force Na potential, but so as not to emulate the action force Z bigger than the most differential pressure force Na potential. That is, by the action force Z, the hub 9 presses and moves the hub stop rib 7d in the opening end 10h of the arrow A side in the direction as shown by the arrow C. That is, the hub stop rib 7d of the small cylindrical portion 7 and the portion near the hub stop rib 7d further expand and deform in the direction as shown by the arrow C. The seal between the hub stop rib 7d and the hub 9 (especially, at the arrow B side) is of course disengaged since the hub stop rib 7d moves in the direction as shown by the arrow C.

In this way, the hub stop rib 7d of the small cylindrical portion 7 and the portion near the hub stop rib 7d are further expanded in the direction as shown by the arrow C further adding the action force Z. On the other hand, the inside diameter in the hub stop rib 7d of the small cylindrical portion 7 broadens by expansion, the hub 9 receiving the force pulling in the direction as shown by the arrow B advances in the direction as shown by the arrow B as the inside diameter broadens. Continuously further adding the action force Z, the hub 9 is advanced to the position where the top end 7e of the hub stop rib 7d abuts on the opening end 10h of the arrow A side, that is, the hub 9 in the outer peripheral face 10i of the main pillar portion 10.

After the hub 9 is advanced to the position where the hub stop rib 7d abuts on the outer peripheral face 10i of the main pillar portion 10, the piston 29 is pulled with the force emulating frictional force in the direction as shown by the arrow A generating at the position where the hub stop rib 7d abuts on the outer peripheral face 10i so as to further advance the hub 9 in the direction as shown by the arrow B, and the hub 9 is pulled until it is completely pulled out of the small cylindrical portion 7 in the direction as shown by the arrow B.

On this occasion, since the outside diameter L1' of the main pillar portion 10 of the hub 9 is smaller than the inside diameter L1 of the hub insertion hole 4b, the contact between the hub 9 and the small cylindrical portion 7 is executed only through the hub stop rib 7d portion, and its pulling operation can be easily executed with a small force after the hub stop rib 7d is disengaged from the hub stop groove 10e.

The piston 29 is further pulled and the needle 26, which is inserted and fixed at the arrow A side of the hub 9, inserts into the hub insertion space 4a from the hole 8a of the end wall 8 in the direction as shown by the arrow B, and further inserts in the inside space 2a of the main cylindrical portion 3 in the direction as shown by the arrow B, and the piston 29 is pulled in the direction as shown by the arrow B such that the top end 26a of the needle 26 is completely inserted into the inside space 2a.

Figure 10:
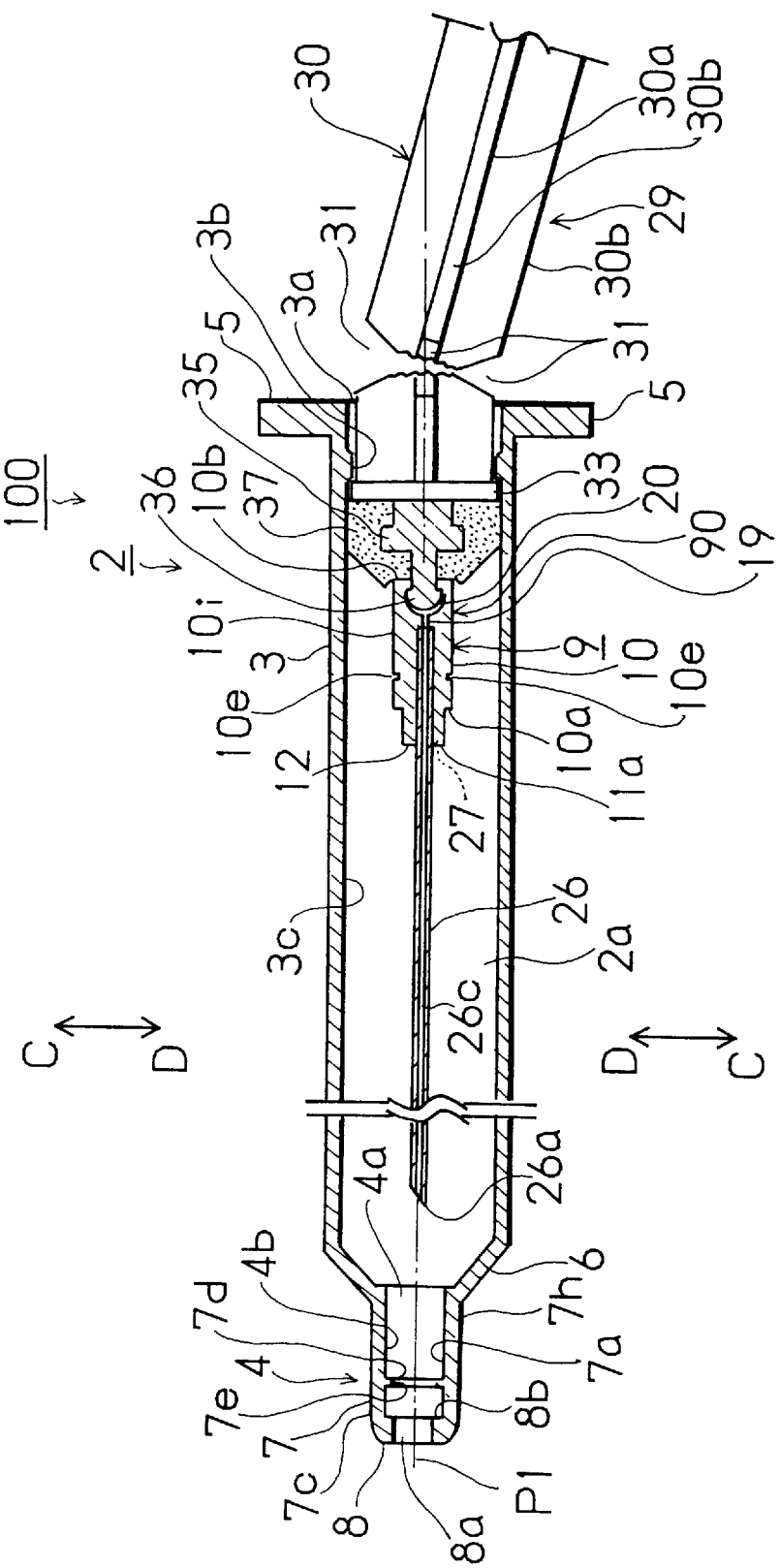
FIG. 10 is a view showing bending and taking of the piston in the syringe assembly as shown in FIG. 1.

The piston 29 is further pulled till the inner press plate 33 abuts on the engagement rib 3b of the main cylindrical portion 3 of the syringe body 2, as shown in FIG. 10, and the piston 29 is stopped.

On this occasion, the inner press plate 33 of the piston 29 is engaged with and stopped by the engagement rib 3b so as to prevent the needle 26 inserted into the hub 9 engaged with the piston 29 from springing to the outside the syringe body 2, by excessively pulling the piston 29 by mistake. In addition, the accident of secondary infection and the like generating from the hurt of hands and the like by the needle 26 can be prevented.

And, in such a state that the inner press plate 33 of the piston 29 is engaged with and stopped by the engagement rib 3b, the position of the notch 31 formed on the piston body 30 of the piston 29 is adjusted to the position of the opening end 3a of the syringe body 2 in the directions as shown by the arrows A and B, as shown in FIG. 10.

Subsequently, while the syringe body 2 is fixed with one hand, the piston 29 is grasped with the other hand, and as shown in FIG. 10, a force in the direction as shown by the arrow C is added to the piston 29. By adding a force in the direction as shown by the arrow C to the piston 29 with respect to the syringe body 2, bending stress is added to the piston body 30 with the engagement rib 3b and the opening end 3a of the syringe body 2 as a supporting point, and then the piston body 30 is broken in the notch 31, which structure is relatively weak with respect to bending stress, of the piston body 30 and the piston body 30 is separated into the arrow A side portion and the arrow B side portion forming a boundary with the notch 31.

By making the engagement rib 3b and the opening end 3a of the syringe body 2 a supporting point, bending stress can be effectively added to the piston body 30 using a principle of a lever. In addition, since the position of the notch 31 is at the position of the opening end 3a, that is, the position of the supporting point, the bending stress adding to the piston body 30 is effectively added to the portion of the notch 31. Therefore, the piston body 30 can be easily bent so as to separate, that is, easily folded and taken.

Subsequently, the portion of the syringe body 2 side folded and taken and the portion of the outer press plate 32 of the piston 29 are disposed of so as to be discarded.

Since the needle 26 is completely inserted and stored in the inside space 2a of the syringe body 2 being held with the top end portion of the piston 29 remaining in the inside space 2a, there is no fear of hurting hands or the like and being secondarily infected from a wound by the needle 26. Therefore, waste disposal can be safely executed. And, the piston 29 is folded and taken, thereby the syringe assembly 1 folded and taken is not bulky, and then waste disposal can be smoothly executed. As described before, the use of the syringe assembly 1 and waste disposal after use all finish.

As described heretofore, the hub 9 of the syringe assembly 1 is inserted into the hub insertion hole 4b, and has a cylindrical hub body 90 through which the hub 9 is pulled from the hub insertion hole 4b to the inside space 2a of the syringe body 2. At the outer periphery portion of the hub body 90, the hub stop groove 10e is annularly formed so as to engage with the inner face of the hub insertion hole 4b. The outside diameter L1' of the portions excluding the hub stop groove 10e of the hub body 90 is smaller than the inside diameter L1 of the portion corresponding to the hub insertion hole 4b. The needle insertion hole 12 in which the needle 26 can be inserted is provided with the end portion 11a of the hub body 90 in the direction of the axis center P1 of the hub body 90. The flow hole 19 is provided with the hub body 90 communicating the needle insertion hole 12 and the inside space 2a of the syringe body 2 with each other in the direction of the axis center P1. At the end portion of the hub body 90, the piston engagement hole 20 is provided capable of engaging with the piston 29.

The connecting structure between the hub 9 and the syringe body 2 is that the hub body 90 of the hub 9 is inserted into the hub insertion hole 4b, and is attachably and detachably inserted so as to be able to be pulled out of the hub insertion hole 4b to the inside space 2a of the syringe body 2. At the inner peripheral face 7a of the hub insertion hole 4b, the hub stop rib 7d is annularly provided, and the hub stop groove 10e of the hub body 9 is provided contacting and engaging with the hub stop rib 7d with a predetermined restoring force Fbc. The gap space 49 is provided between the inner periperal face 7a of the hub insertion hole 4b excluding the hub stop rib 7d and the outer peripheral face 10i of the hub body 90. The gap allows the hub 9 to be extremely easily pulled to the inside space 2a.

In addition, the connecting structure between the hub 9 and the syringe body 2 is comprised such that the width L4' of the hub stop groove 10e is different from the width L4 of the hub stop rib 7d.

And, the syringe assembly 1 has the syringe body 2 and the hub 9 comprising the connecting structure, the piston 29 is movably provided in the main cylindrical portion 3 of the syringe body 2 in the direction of the axis center P1 with respect to the main cylindrical portion 3 occupying the inside space 2a of the main cylindrical portion 3 in the direction of the axis center P1, the hub engagement portion 36 is provided with the piston 29 so as to engage with the piston engagement hole 20 of the hub 9 facing the piston engagement hole 20. The needle 26 is provided with the needle insertion hole 12 of the hub 9.

In addition, the piston 29 of the syringe assembly 1 is comprised in such a manner that the piston body 30 can be bent and taken between the outer press plate 32 and the inner press plate 33.

In addition, the engagement rib 3b is provided with the main cylindrical portion 3 of the syringe assembly 1 so as not to pull the inner press plate 33 of the piston 29 out of the main cylindrical portion 3.

In addition, the notch 31 is formed so as to position at the opening end 3a of the main cylindrical portion 3 when the piston 29 abuts on the engagement rib 3b.

Furthermore, when the syringe assembly 1 is assembled, the hub 9 is disposed elastically engaging the hub stop groove 10e of the hub 9 with the hub stop rib 7d of the hub insertion portion 4, the piston 29 is inserted into the syringe body 2, and the needle 26 is inserted into and contacted with the needle insertion hole 12 of the hub 9. The hub 9 are the needle 26 can be off course together inserted into and attached to the hub insertion portion 4 in such a state that the needle 26 is attached to the hub 9 in advance.

After use of the syringe assembly 1, the hub 9 and the piston 29 are engaged with each other by the operation of the piston 29 in the direction of the axis center P1 in the piston engagement hole 20 and the hub engagement portion 36, and furthermore, the hub 9 and the needle 26 attached to the hub 9 are inserted into the inside space 2a of the syringe body 2 by the operation of the piston 29 in the direction of the axis center P1.

After the hub 9 and the needle 26 attached to the hub 9 are inserted into the inside space 2a of the syringe body 2, the piston 29 is supported with the syringe body 2 in the engagement rib 3b and the opening end 3a when the piston 29 is folded so as to be taken, and therefore, a principle of a lever can be applied.

Furthermore, in case of assembly of the syringe assembly 1, the hub 9 of the syringe assembly 1 is pressed in the direction of the axis center P1 so as to insert into and attach to the hub insertion hole 4b.

Accordingly, in the hub 9, the connecting structure of the hub 9 and the syringe assembly 1 using the hub 9, by setting a predetermined restoring force Fbc as a desired size, the state of inserting the hub 9 into the hub insertion hole 4b can be maintained while the syringe assembly 1 is used, and the insertion state is by two sealing points such that the hub stop groove 10e and the hub stop rib 7d are contacted in two points. That is, water tight or air tight between the hub 9 and the syringe body 2 is extremely increased while the syringe assembly 1 is used.

The syringe assembly 1 may be comprised in such a manner that a plurality of slits 50 are formed in the hub insertion portion 4 of the syringe assembly 1.

Figure 11:
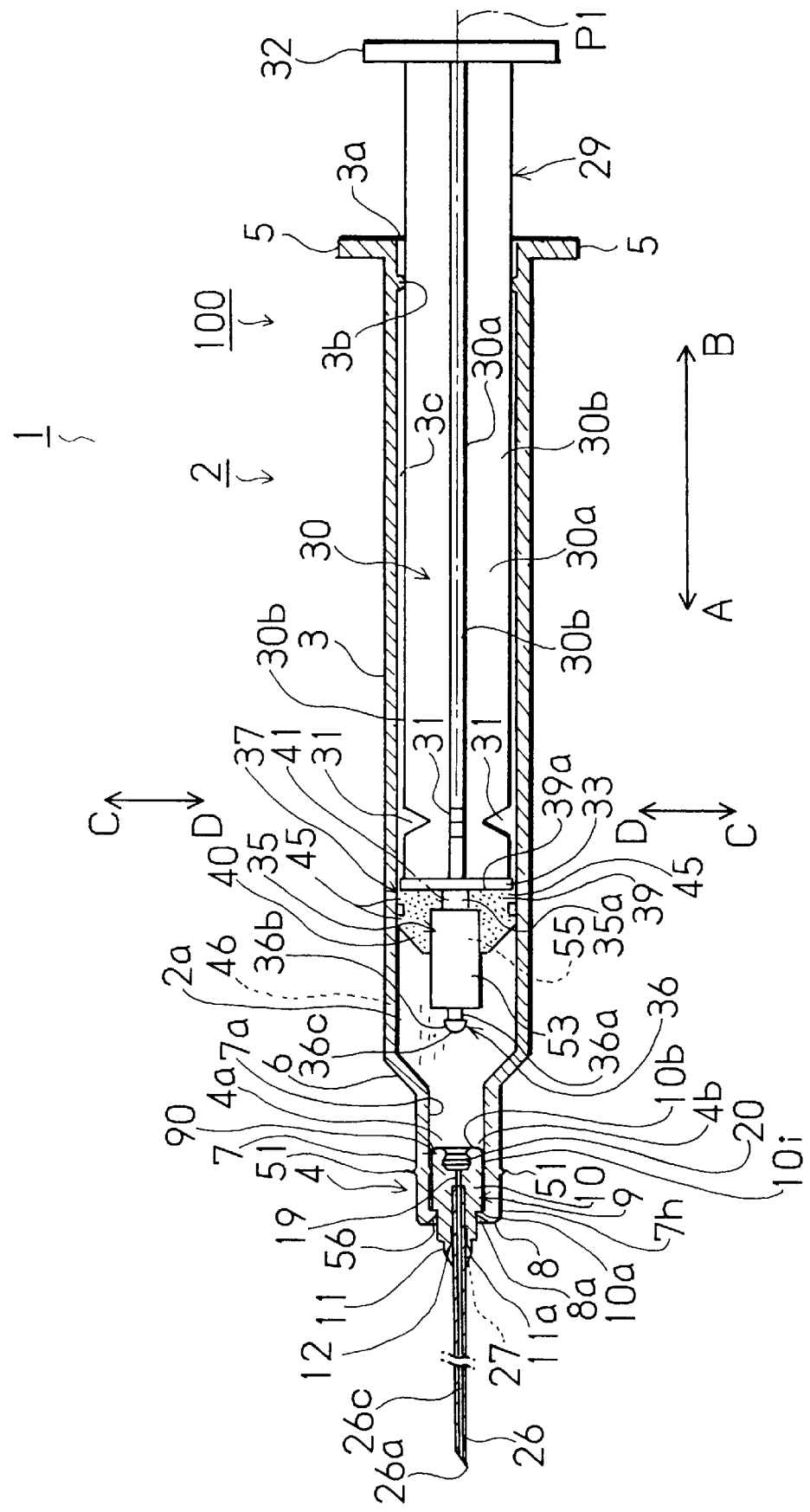
FIG. 11 is a typical sectional view showing an example of the syringe assembly having slits in the syringe of the syringe assembly according to the present invention.

That is, the syringe assembly 1 in which the slits 50 are formed, has the syringe 100 comprising the syringe body 2 and the syringe support 5, and in the syringe body 2, the main cylindrical portion 3, in which the engagement rib 3b is provided at the inner peripheral face 3c side, taper 6 and the hub insertion portion 4 are unitedly provided, similar to the syringe assembly 1 in which no slit 50 is provided in the first embodiment above mentioned, as shown in FIG. 11.

In the syringe assembly 1 in which the slits 50 are provied, the hub insertion portion 4 is comprised as follows.

Figure 13:
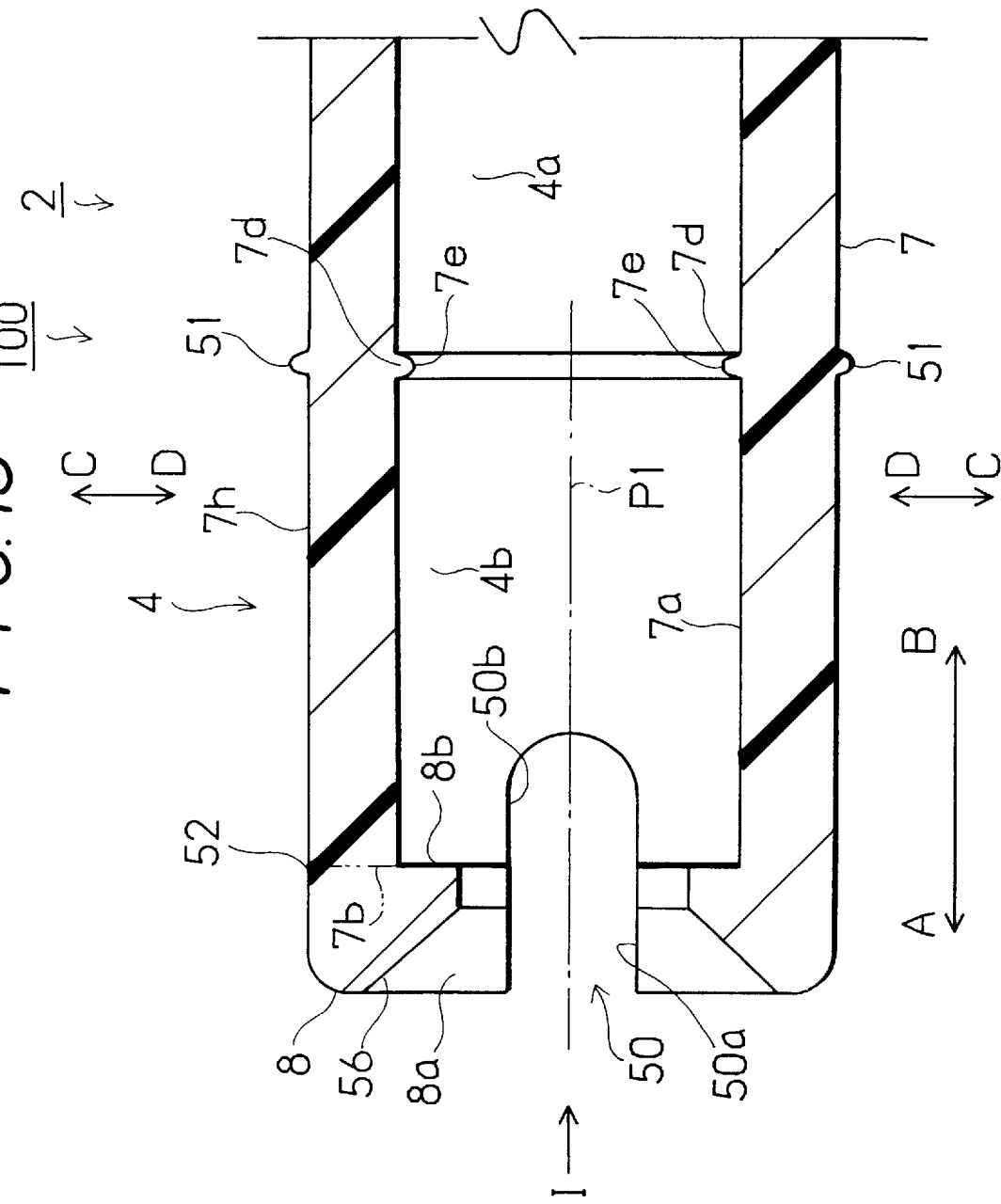
FIG. 13 is a view showing the portion near the hub insertion portion as shown in FIG. 11 in a natural state.
Figure 16:
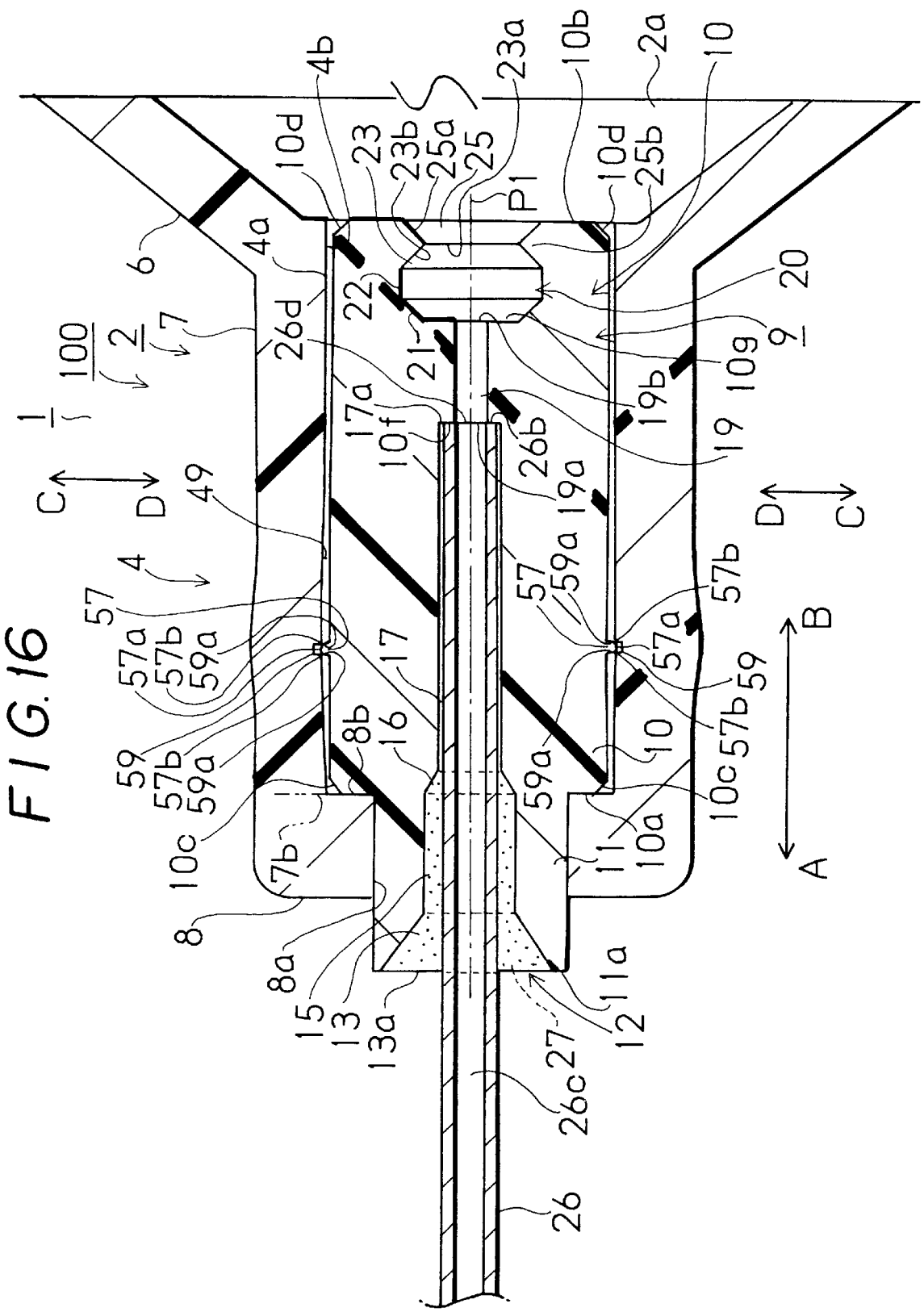
FIG. 16 is an enlarged sectional view of the portion near the hub in an example of the syringe assembly in which a seal rib is formed at the hub side and a seal groove is formed at a hub insertion hole side, of the syringe assembly according to the present invention.

That is, the hub insertion portion 4 has the small cylindrical portion 7 which is provided being united with the taper 6 and the end wall 8 which is provided being united with the small cylindrical portion 7 at the end portion 7b side of the small cylindrical portion 7, as shown in FIG. 13 or 16. The inside of the small cylindrical portion 7 is the hub insertion hole 4b. The hub stop rib 7d is annularly provided at the inner peripheral face 7a side of the small cylindrical portion 7, that is, at the inner peripheral face 7a side of the hub insertion hole 4b, and the section of the hub stop rib 7d is formed in the shape of a circular arc. A stiffening rib 51 is annularly provided at the outer peripheral face 7h side of the small cylindrical portion 7 at the position corresponding to the hub stop rib 7d putting the small cylindrical portion 7 therebetween (No rib 51 may be formed.)

The hole 8a is provided with the end wall 8 penetrating the end wall 8 in the directions as shown by the arrows A and B, and the hole 8a is taperingly formed in such a manner that its inside diameter is made bigger for the direction as shown by the arrow A.

Figure 14:
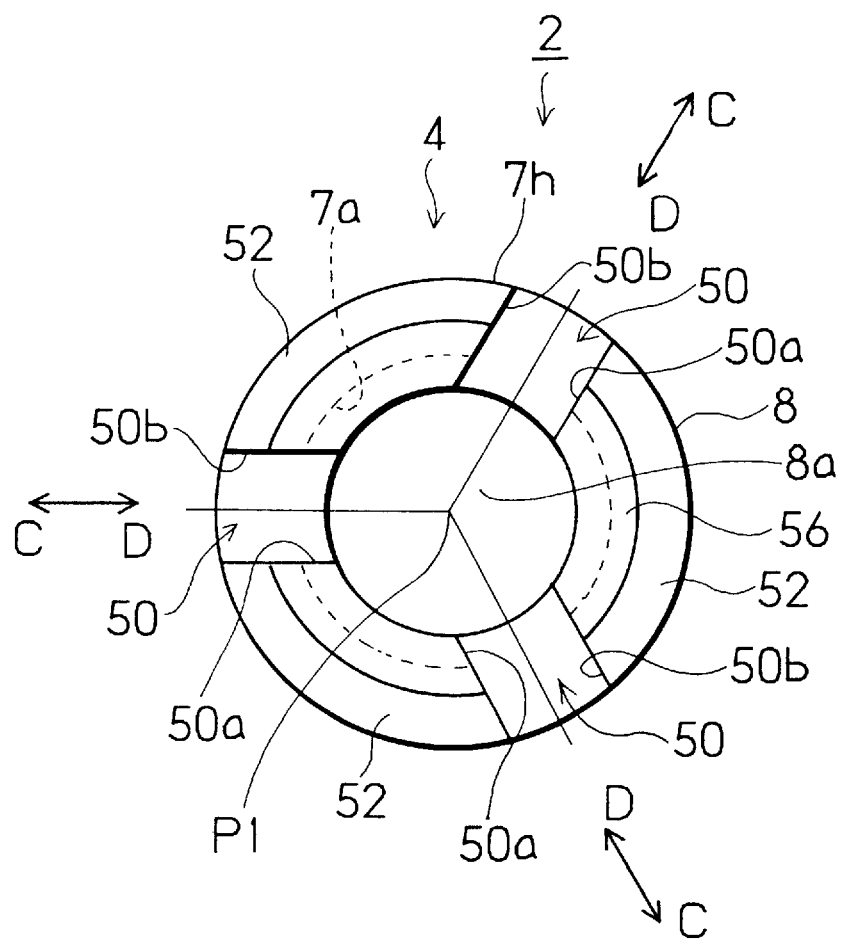
FIG. 14 is a view in the direction of the arrow I of FIG. 13.

Three first slits 50a are formed at the end wall 8 extending in a radial direction with respect to the axis center P1, that is, in the directions as shown by the arrows C and D in FIG. 14. These three first slits 50a are formed at 120° pitch being equivalent to each other with the axis center P1 as its center. The three first slits 50a respectively communicate with the hole 8a keeping in the hole 8a provided with the end wall 8.

On the other hand, three second slits 50b are formed at the small cylindrical portion 7 paralel to the directions as shown by the arrows A and B. The second slits 50b are formed at the arrow A side rather than the hub stop rib 7d and the stiffening rib 51 such that they don't reach the hub stop rib 7d and the stiffening rib 51. In addition, the three second slits 50b are formed corresponding to the three first slits 50a. The three second slits 50b and the three first slits 50a are united at the boundary portion between the small cylindrical portion 7 and the end wall 8 such that the corresponding two are communicated with each other and contacted with each other. The first slit 50a and the second slit 50b which are communicated and contacted with each other are the slit 50, and the hub insertion portion 4, in which three slits 50 are formed, is divided into three hub insertion portion pieces 52 at the arrow A side of the end wall 8 and the small cylindrical portion 7.

Figure 12:
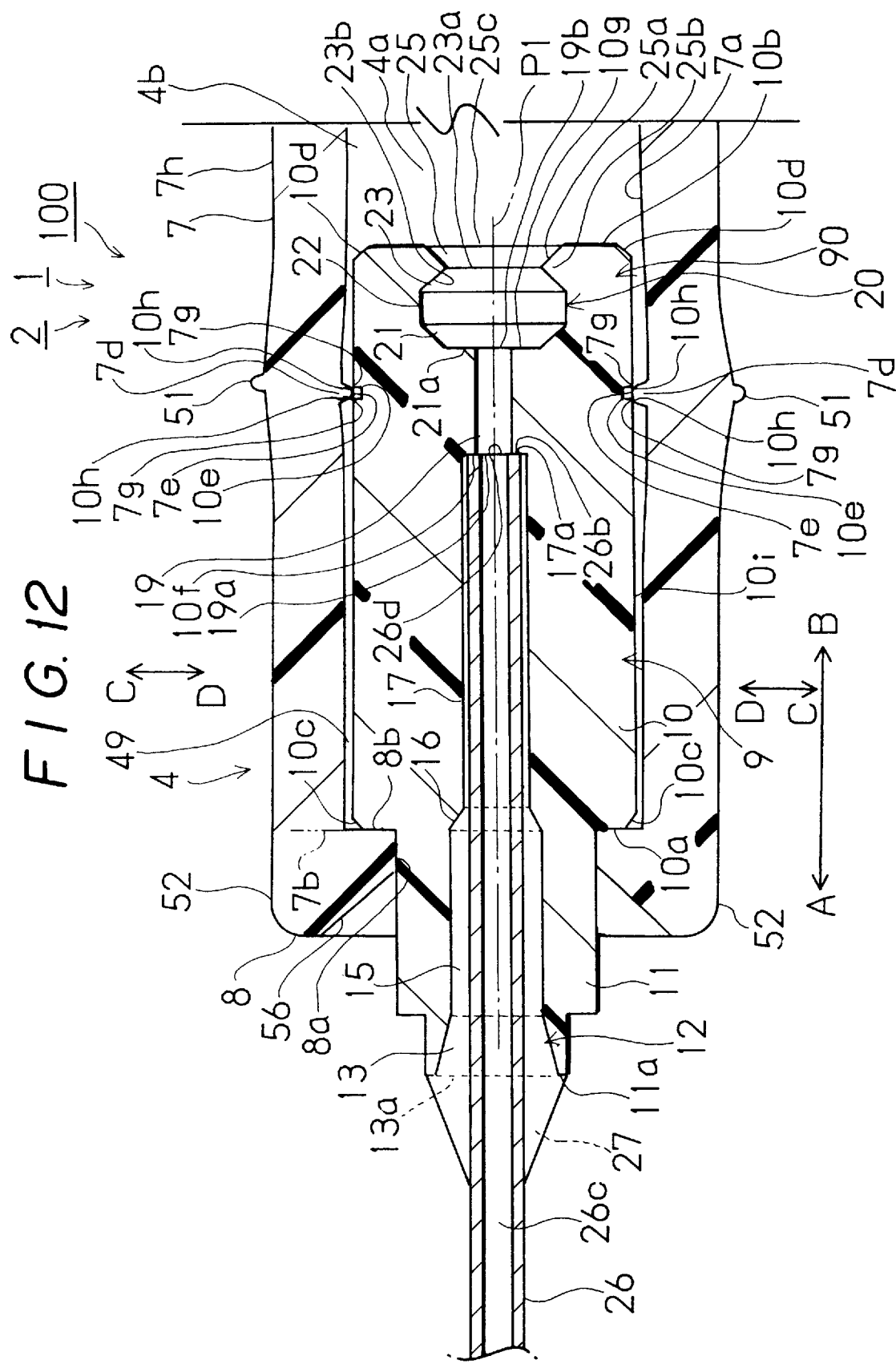
FIG. 12 is an enlarged sectional view in the portion near the hub of the syringe assembly as shown in FIG. 11.

As shown in FIG. 12, the hub 9 of the syringe assembly 1, in which the slits 50 are provided, has a hub body 90. The main pillar portion 10, which outside diameter is smaller than the inside diameter of the small cylindrical portion 7, is provided with the hub body 90. The hub stop groove 10e is annularly formed at the outer peripheral face 10i side of the main pillar portion 10. The width of the hub stop groove 10e in the directions as shown by the arrows A and B is narrower than one of the hub stop rib 7d in the directions as shown by the arrows A and B.

The small pillar portion 11 is provided at the arrow A side of the main pillar portion 10. The needle insertion hole 12, which is comprised of the first taper hole 13, the first cylindrical hole 15, the second taper hole 16 and the second cylindrical hole 17 in the direction as shown by the arrow B from the end face 11a of the arrow A side of the small pillar portion 11, is provided with the hub 9.

The flow hole 19 is provided with the hub 9 at the arrow B side of the needle insertion hole 12, communicating with the needle insertion hole 12 in the directions as shown by the arrows A and B. At the arrow B side of the flow hole 19, the piston engagement hole 20 is provided communicating with the flow hole 19 in the directions as shown by the arrows A and B. The piston engagement hole 20 is comprised of the first taper hole 21, the cylindrical hole 22 and the second taper hole 23, and the piston engagement hole 20 is formed such that the flow hole 19 communicates with the inside of the hub insertion hole 4b, that is, the hub insertion space 4a in the directions as shown by the arrows A and B.

As shown in FIG. 12, in the hub insertion portion 4 of the syringe assembly 1, in which the slits 50 are provided, the small cylindrical portion 7 of the hub insertion portion 4 elastically expands in the hub stop rib 7d and the near portion thereof in the direction as shown by the arrow C, and the hub 9 is inserted into the hub insertion hole 4b of the hub insertion portion 4 elastically expanded. The hub 9 is inserted such that the main pillar portion 10 is inserted into the hub insertion hole 4b and the small pillar portion 11 is inserted into the hole 8a of the end wall 8. The end face 10a of the arrow A side of the main pillar portion 10 and the wall face 8b of the arrow B side of the end wall 8 closely contact with each other. The hub stop rib 7d of the small cylindrical portion 7 and the hub stop groove 10e of the main pillar portion 10 are at the positions which adjust and correspond to each other. Therefore, the hub stop rib 7d engages with the hub 9 in such a manner that the top end 7e of the hub stop rib 7d is inserted into the hub stop groove 10e in the direction as shown by the arrow D and the seal portions 7g, 7g of both sides of the top end 7e of the hub stop rib 7d and the opening ends 10h, 10h of both sides of the hub stop groove 10e respectively linearly abut on each other along the outer periphery of the hub 9.

On this occasion, the position of the end face 10b of the arrow B side of the hub 9 inserted into the hub insertion hole 4b is near the middle portion of the small cylindrical portion 7 in the directions as shown by the arrows A and B, as shown in FIG. 11.

Figure 15:
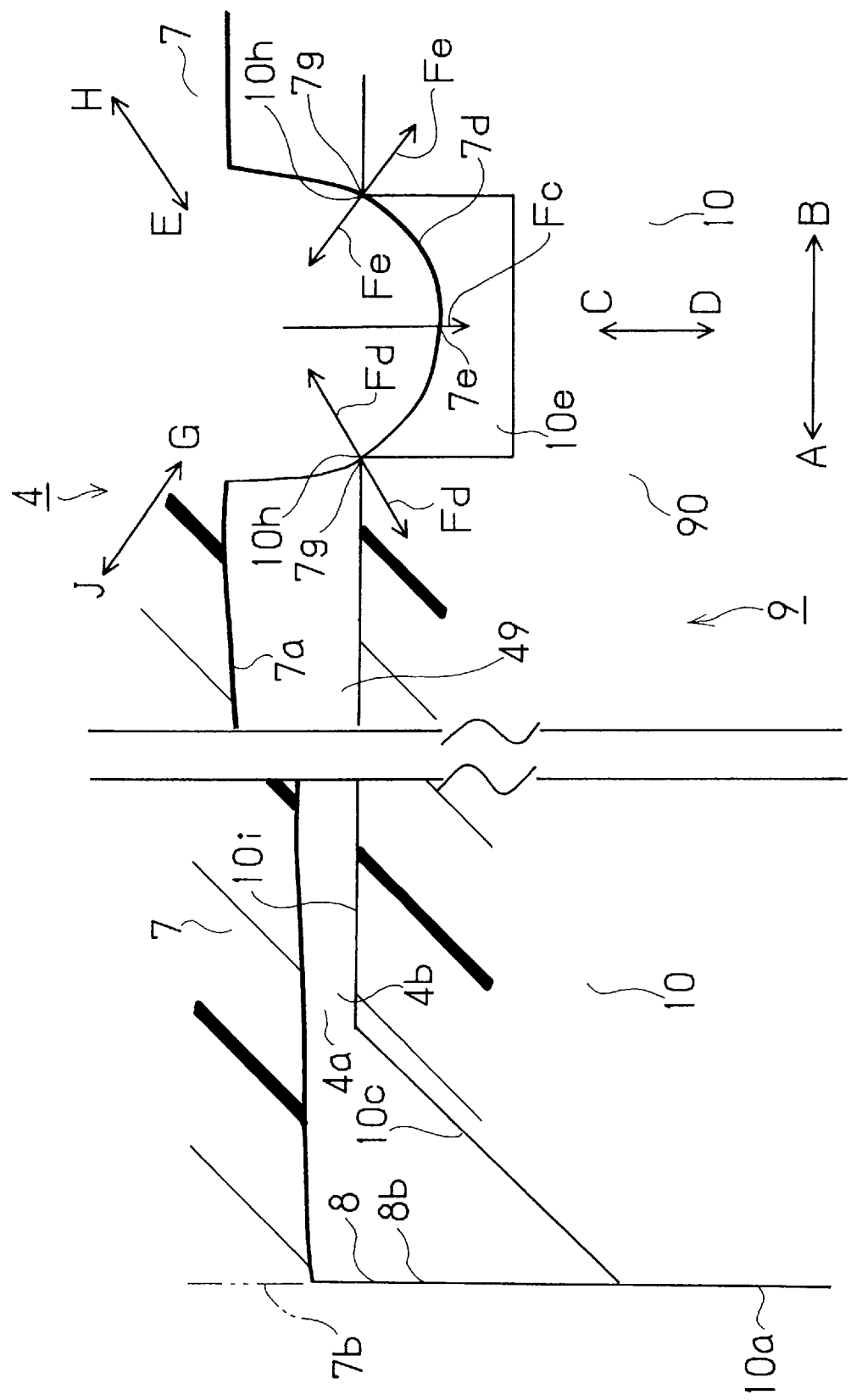
FIG. 15 is a view showing dynamical relation between the hub insertion portion and the hub as shown in FIG. 12.

Since the hub stop rib 7d and the near portion thereof are expanded in the direction as shown by the arrow C due to elastic deformation, a predetermined restoring force Fc in the direction as shown by the arrow D is added on the hub stop rib 7d, as shown in FIG. 15 (Since the small cylindrical portion 7 don't deform in the directions as shown by the arrows A and B, the restoring forces Fa, Fb and the like, which were explained in the first embodiment, are not applied between the end wall 8 and the hub 9 or between the hub stop rib 7d and the hub 9.).

That is, by the restoring force Fc, the portions which the hub 9 abuts on the hub stop rib 7d at the arrows A and B sides (that is, respective opening ends 10h, 10h and the respective seal portions 7g, 7g at the arrows A and B sides) balance in the abutting portions such that the seal pressures Fd, Fd and the seal pressures Fe, Fe are respectively added, that is, such that the abutting portions are sealed.

Then, the portion between the respective seal portions 7g, 7g of the arrows A and B sides of the hub stop rib 7d and the respective opening ends 10h, 10h of the arrows A and B sides of the hub 9 is sealed in the section of FIG. 15 with point contact, and the portion is in high water tight state (or air tight state) similar to FIG. 4.

On this occasion, the restoring force Fc can be preset as a desired size one according to the material of the hub insertion portion 4, the wall thickness of the small cylindrical portion 7 and the positions of the hub stop rib 7d and the hub stop groove 10e.

The rigidity of the hub stop rib 7d and the near portion thereof is increased in the small cylindrical portion 7 by the stiffening rib 51 which is at the position corresponding to the hub stop rib 7d putting the small cylindrical portion 7 therebetween, and therefore, a predetermined restoring force Fc can be effectively obtained.

On the other hand, in the hub 9 of the syringe assembly 1, in which the slits 50 are provided, as shown in FIG. 11 or 12, the needle 26 is inserted into the needle insertion hole 12, and the adhesive 27 is filled between the hub 9 and the needle 26 in the needle insertion hole 12 such that both are firmly bonded to each other.

As shown in FIG. 11, the piston 29 of the syringe assembly 1, in which the slits 50 are provided, has the bar-shaped piston body 30 extending in the directions as shown by the arrows A and B formed crossing the plate portions 30a and 30a. The four notches 31 are formed at the plate portions 30a, 30a of the piston body 30 from the respective both sides portions. The outer press plate 32 is provided with the piston body 30 at the arrow B side, and the inner press plate 33 is provided at the arrow A side. At the arrow A side of the inner press plate 33, the packing support 35 is provided. The circular cylindrical portion 35a, which is provided being united with the inner press plate 33, is provided with the packing support 35. At the arrow A side of the circular cylindrical portion 35a, an insertion cylindrical portion 53, which outside diameter is equal to one of the hub insertion hole 4b, is provided. At the arrow A side of the insertion cylindrical portion 53, the hub engagement portion 36 is provided. The circular cylindrical portion 36a, which is provided united with the insertion cylindrical portion 53, is provided with the hub engagement portion 36. At the arrow A side of the circular cylindrical portion 36a, the insertion portion 36b in a semi-spherical shape is provided.

The packing 37 is provided with the piston 29, and the packing 37 has the circular cylindrical portion 39 at which outer periphery portion the folds 45 are formed, and at the top end side of the circular cylindrical portion 39 (the arrow A side), the taper 40 is formed. The first hole 41, which inside diameter is equal to the outside diameter of the circular cylindrical portion 35a of the packing support 35, is provided with the packing 37 for the taper 40 from the end face 39a of the circular cylindrical portion 39 side. A second hole 55, which inside diameter is equal to the outside diameter of the insertion cylindrical portion 53 of the packing support 35, is provided with the packing 37 communicating with the first hole 41 at the arrow A side. The second hole 55 is open at the taper 40 side. The length of the first hole 41 in the directions as shown by the arrows A and B is equal to one of the circular cylindrical portion 35a in the directions as shown by the arrows A and B, and the length of the second hole 55 in the directions as shown by the arrows A and B is shorter than one of the insertion cylindrical portion 53 in the directions as shown by the arrows A and B.

The packing 37, which is comprised as described heretofore, is attached to the packing support 35 such that the circular cylindrical portion 35a of the packing support 35 is inserted into the first hole 41 and the insertion cylindrical portion 53 of the packing support 35 is inserted into the second hole 55.

The piston 29 attached the packing 37 thereto is inserted into the main cylindrical portion 3 of the syringe body 2 facing the packing 37 to the arrow A side. And, the folds 45 of the packing 37 and the circular cylindrical portion 39 are inserted into the main cylindrical portion 3 in such a manner that they are elastically reduced in the direction as shown by the arrow D. The inner peripheral face 3c of the main cylindrical portion 3 is smooth, and then the piston 29 is slidably inserted into the syringe body 2.

The syringe assembly 1, in which the slits 50 are provied, is comprised as described heretofore, and then, the assembly of the syringe assembly 1 is executed as follows.

At first, the first hole 41 of the packing 37 is broadened making use of flexibility of the packing 37, and after that, the hub engagement portion 36 side of the piston 29 is inserted from the first hole 41 side of the packing 37 for the direction as shown by the arrow A till the circular cylindrical portion 35a of the packing support 35 is inserted into the first hole 41 and the insertion cylindrical portion 53 of the packing support 35 is inserted into the second hole 55, as shown in FIG. 11 (The insertion cylindrical portion 53 is inserted into the second hole 55 in only a part of the arrow B side.).

Thereafter, the insertion of the packing 37 finishes after a hand or the like with which the first hole 41 is broadened is left therefrom so as to return the packing 37 to a natural state. subsequently, the piston 29 attaching the packing 37 thereto is inserted into the syringe body 2.

The insertion of the piston 29 is executed in such a manner that the side attached the packing 37 of the piston 29 is inserted into the inside space 2a of the syringe body 2 from the opening end 3a side of the syringe body 2 and the circular cylindrical portion 39 of the packing 37 and the outside diameter of the folds 45 are reduced by pressing the piston 29 in the direction as shown by the arrow A.

That is, the piston 29 is inserted into the main cylindrical portion 3 while the packing 37 is reduced and deformed by pressing the piston 29 in the direction as shown by the arrow A, and the piston 29 is inserted to the position, where the taper 40 of the packing 37 is inserted into the inside of the taper 6 of the syringe body 2 so as to adjust to each other, and then the insertion of the piston 29 finishes.

In such a state that the taper 40 of the packing 37 is inserted into the inside of the taper 6 of the syringe body 2 so as to adjust to each other, the insertion cylindrical portion 53 of the packing support 35 of the piston 29 is inserted in the hub insertion hole 4b of the hub insertion portion 4.

Subsequently, the hub 9 is inserted into the hub insertion hole 4b from the hole 8a side of the end wall 8 of the hub insertion portion 4.

That is, the end face 10b of the arrow B side of the hub 9 is adjusted to the hole 8a of the end wall 8, and in the afore-mentioned state, the hub 9 is pressed in the direction as shown by the arrow B. At the end wall 8 side of the hub insertion portion 4, the three slits 50 are provided as described heretofore, and the end wall 8 side of the hub insertion portion 4 is divided into the three hub insertion portion pieces 52. In addition, by pressing, the chamfer portion 10c of the hub 9 abuts on a tapered wall face 56 facing the hole 8a of the end wall 8, and then the action force for elastically bending and deforming the hub insertion portion pieces 52 in the direction as shown by the arrow C is applied to the three hub insertion portion pieces 52. The hub insertion portion piece 52 is easy to be elastically bent and deformed in the direction as shown by the arrow C against the action force in the direction as shown by the arrow C for its construction in comparison with the cylindrical portions and the like not divided of the small cylindrical portion 7. Therefore, as the hub 9 is pressed, the hub insertion portion piece 52 is elastically bent and deformed in the direction as shown by the arrow C and the diameter of the hole 8a is broadened.

The hub 9 is further pressed so as to elastically bend and deformed the hub insertion portion piece 52 and the diameter of the hole 8a is broadened to the outside diameter of the main pillar portion 10 of the hub 9 so as to insert the hub 9 into the hub insertion hole 4b from the main pillar portion 10. The hub 9 is further pressed so as to completely insert the main pillar portion 10 into the hub insertion hole 4b, and the insertion of the hub 9 by pressing is stopped at the position where the end face 10a of the main pillar portion 10 of the hub 9 is closely contacted with the wall face 8b of the arrow B side of the end wall 8.

At the position where the end face 10a of the main pillar portion 10 is closely contacted with the wall face 10a of the end wall 8, the small pillar portion 11 is penetratingly inserted into the hole 8a, which smallest diameter is slightly bigger rather than the outside diameter of the small pillar portion 11.

On this occasion, the hub stop rib 7d of the hub insertion portion 4 and the hub stop groove 10e of the hub 9 are at the positions which correspond to and adjust to each other, as described heretofore, and engage with each other so as to abut on each other by the seal portions 7g, 7g of the hub stop rib 7d and the opening ends 10h, 10h of the hub stop groove 10e.

As described heretofore, the insertion of the hub 9 into the syringe body 2 finishes. On this occasion, the hub 9 is fixed by the hub insertion portion 4 balancing respective forces between the hub stop groove 10e of the hub 9 and the hub stop rib 7d of the small cylindrical portion 7, as described heretofore.

In addition, the hub 9 exists such that the spherical surface 36c side of the insertion portion 36b of the engagement portion 36 of the piston 29 contacts with the wall face 25a facing the third taper hole 25 of the piston engagement hole 20 provided with the hub 9.

The insertion operation of the hub 9 into the syringe body 2 can be executed only by pressing the hub 9, and therefore, it is easy with no complex assembly operation.

Subsequently, the needle 26 is inserted into the needle insertion hole 12 of the hub 9 so as to bond. That is the needle 26 is inserted into the needle insertion hole 12 from the rear end 26b side of the needle 26 in the direction as shown by the arrow B, as shown in FIG. 12 till the rear end 26b abuts on the innermost wall face 10f of the hub 9 of the needle insertion hole 12. After insertion, the space between the hub 9 and the needle 26 in the needle insertion hole 12 is filled with the adhesive 27 so as to harden the adhesive 27, the insertion of the needle 26 to the hub 9 finishes.

The end of the insertion of the needle 26 means the end of assembly of the syringe assembly 1, in which the slits 50 are provided. The needle 26 is in advance attached to the hub 9, and in this state the hub 9 attached the needle 26 thereto may be attached to the syringe body 2.

As described heretofore, the assembly of the syringe assembly 1, in which the slits 50 are provided, is easy with no complex operation since the most operations (that is, all the operations excluding the operation of the inserting and fixing the needle 26) are executed by pressing.

Furthermore, since the hub 9 is inserted after the piston 29 is inserted into the syringe body 2, dust entry into the inside space 2a is extremely saved while the hub 9 is inserted.

The syringe assembly 1, in which the slits 50 are provided, is comprised as described heretofore, and is assembled as explained before. The method of disposal after using the syringe assembly 1 is almost similar to one of the syringe assembly 1 having no slits 50 in the first embodiment.

As described heretofore, the connecting structure between the hub 9 and the syringe body 2 in the syringe assembly 1 having the slits 50 is comprised in such a manner that the hub body 90 of the hub 9 can be inserted into the hub insertion hole 4b from the hole 8a side of the end wall 8.

In addition, in case of the connecting structure between the hub 9 and the syringe body 2 is comprised in such a manner that three slits 50 are formed at the periphery of the hole 8a of the hub insertion portion 4.

In addition, in case of the assembly of the syringe assembly 1, the piston 29 is inserted into the syringe body 2, the hub 9 is inserted into the hub insertion hole 4b from the hole 8a side of the end wall 8, and then, the hub 9 is positioned such that the hub stop groove 10e of the hub 9 elastically engages with the hub stop rib 7d of the hub insertion portion 4 each other, and the needle 26 is inserted into and contacted with the needle insertion hole 12 of the hub 9 (or the hub 9 attached the needle 26 thereto is inserted into the hub insertion hole 4b).

Therefore, in case of assembly of the syringe assembly 1, the hub 9 of the syringe assembly 1 is inserted into the hub insertion hole 4b pressing and inserting from the hole 8a side for the direction of the axis center P1, and is inserted without passing the inside space 2a of the syringe body 2.

Therefore, the main cylindrical portion 3 of the syringe body 2 and the like do not extremely electrify static electricity and dust entry into the inside space 2a is extremely saved.

The hub 9 as explained in the above-mentioned first and second embodiments is comprised in such a manner that the seal portion of the hub 9 is a groove, that is, the hub stop groove 10e.

However, any kind of formation of the seal portion of the hub 9 is allowable as long as it is annularly formed at the outer peripheral face 10i side of the hub body 90 of the hub 9 and is formed capable of engagaging with the inner face of the hub insertion hole 4b. Therefore, the seal portion of the hub 9, which is formed in the shape of a projection may be allowable, as shown in FIG. 16, 17 or 18.

In the embodiment as shown in FIG. 16, the hub 9 to be inserted into the hub insertion hole 4b, in which an annular seal groove 59 is provided at the inner face of the hub insertion hole 4b, is comprised in such a manner that a seal rib 57, which is annularly formed at the outer peripheral face 10i side of the main pillar portion 10 of the hub 9, and which has the width broader than one of the seal groove 59, is provided (The slits 50 may be provided in the hub insertion hole 4b.).

Therefore, the connecting structure of the hub 9 to the syringe body 2 is that the main pillar portion 10 of the hub 9 is inserted into the hub insertion hole 4b, and is attachably and detachably inserted so as to pull out the hub insertion hole 4b into the main cylindrical portion 3, and the seal rib 57 of the main pillar portion 10 contacts and engages with the seal groove 59 of the hub insertion hole 4b with a predetermined seal pressure maintaining the sealing state with a point contact in the section of FIG. 16 abovementioned. In addition, the gap space 49 is formed between the inner peripheral face 7a of the hub insertion hole 4b excluding the seal groove 59 and the main pillar portion 10.

Figure 17:
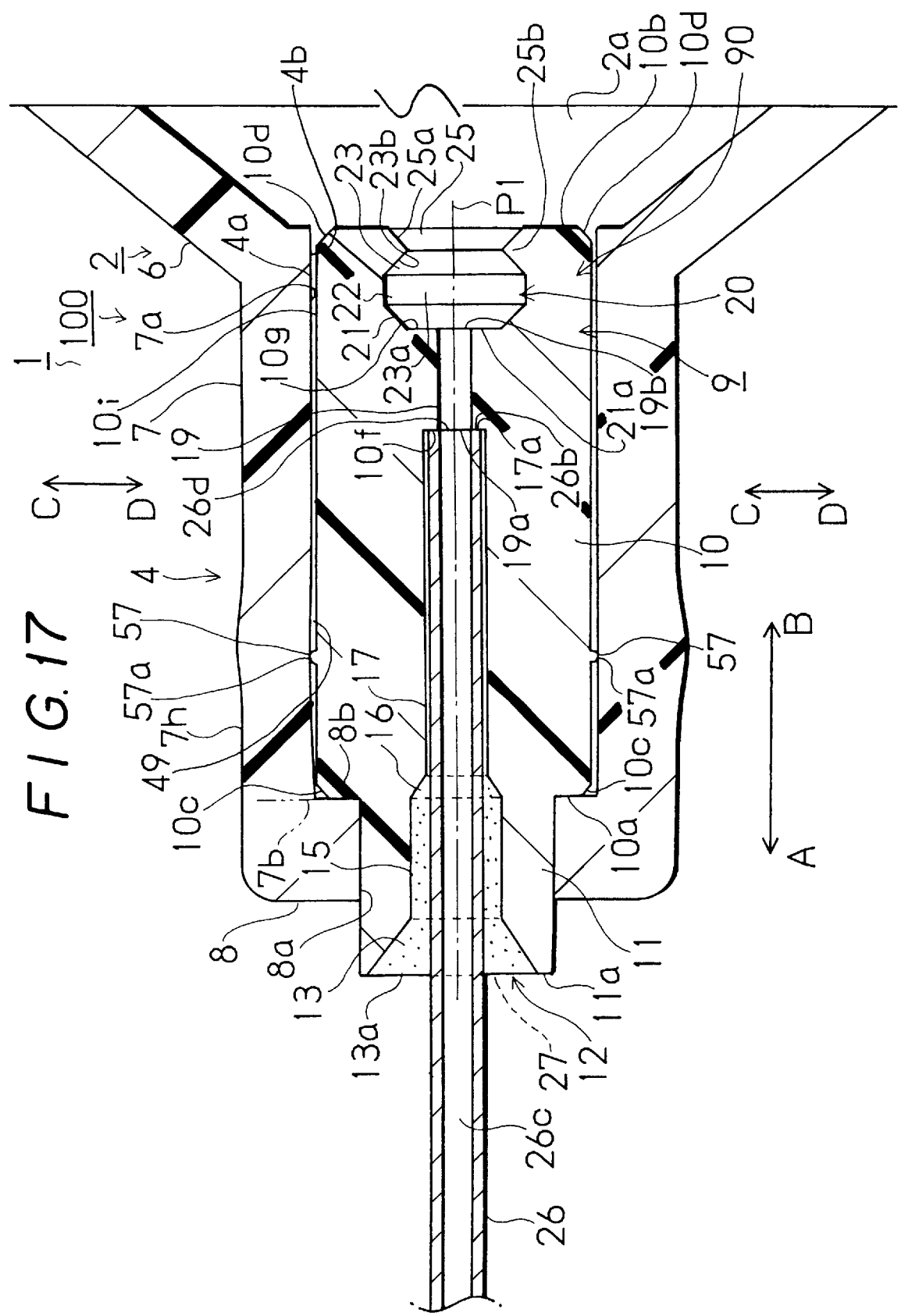
FIG. 17 is an enlarged sectional view of the portion near the hub in an example of the syringe assembly the seal rib is formed at the hub side and a hub seal portion of the hub insertion hole side corresponds with the inner peripheral face of the hub insertion hole, of the syringe assembly according to the present invention.
Figure 18:
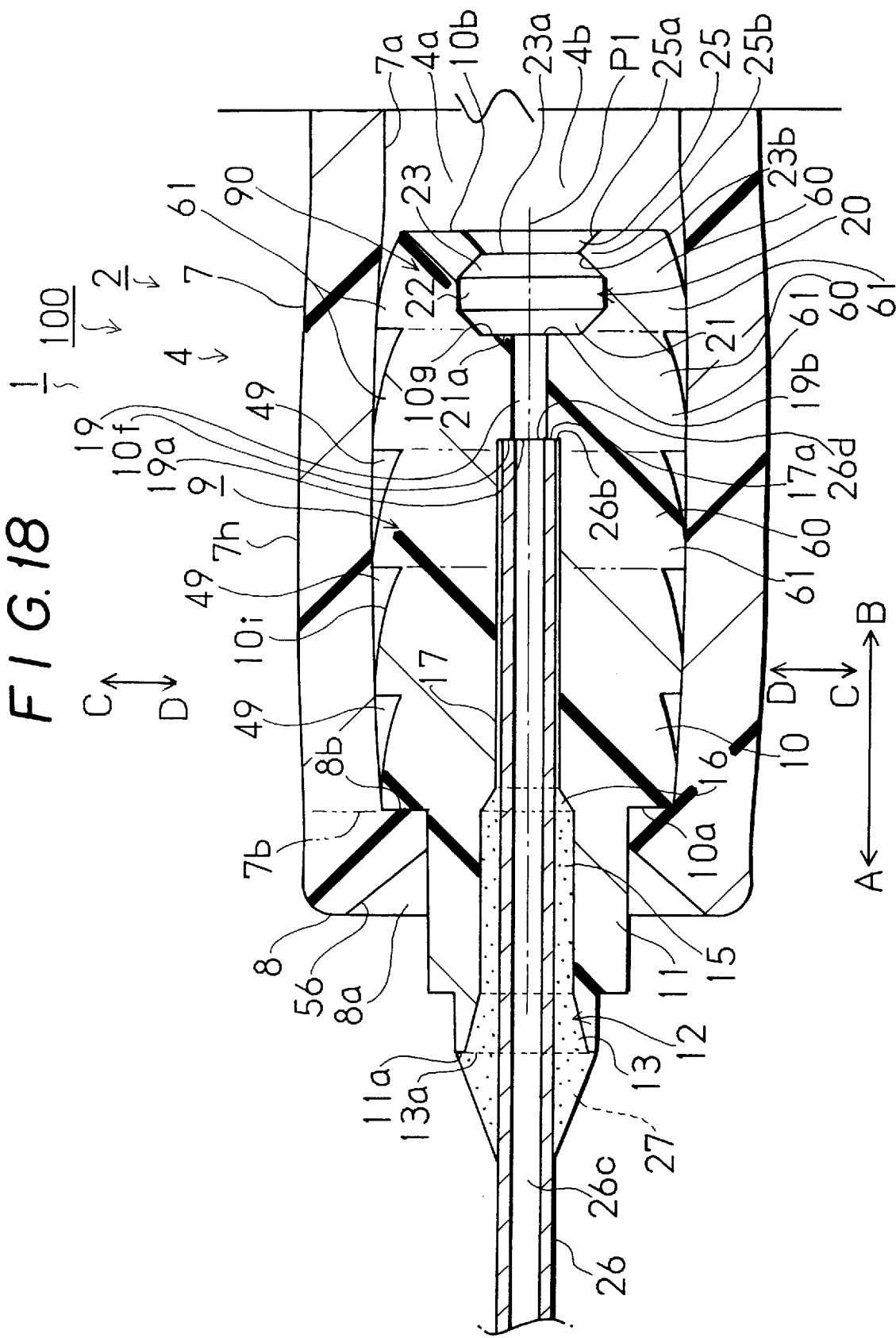
FIG. 18 is an enlarged sectional view of the portion near the hub in an example of the syringe assembly in which fold portions are formed at the hub side and the hub seal portion of the hub insertion hole side corresponds with the inner peripheral face of the hub insertion hole, of the syringe assembly according to the present invention.

In the embodiment as shown in FIG. 17, the hub 9 to be inserted into the hub insertion hole 4b, at which inner peripheral face 7a the hub seal portion is formed on the same plane as the inner peripheral face 7a, that is, no groove and no projection is formed on the inner face of the hub insertion hole 4b, is comprised in such a manner that the seal rib 57 is annularly provided at the outer peripheral face 10i side of the main pillar portion 10 of the hub 9 (The slits 50 may be provided in the hub insertion hole 4b.).

Therefore, the connecting structure of the hub 9 to the syringe body 2 is that the main pillar portion 10 of the hub 9 is inserted into the hub insertion hole 4b, and is attachably and detachably inserted so as to pull out the hub insertion hole 4b into the main cylindrical portion 3, and the seal rib 57 of the main pillar portion 10 contacts and engages with the inner peripheral face 7a of the hub insertion hole 4b with a predetermined seal pressure. In addition, the gap space 49 is formed between the inner peripheral face 7a of the hub insertion hole 4b and the main cylindrical portion 10 excluding the seal rib 57.

In the embodiment as shown in FIG. 18, the hub 9 to be inserted into the hub insertion hole 4b, at which inner peripheral face 7a the hub seal portion is formed on the same plane as the inner peripheral face 7a, that is, no groove and no projection is formed on the inner face of the hub insertion hole 4b, is comrised as follows.

That is, the main pillar portion 10 of the hub 9 is imaginarily comprised by a plurality of tapered main pillar portion pieces 60 (the number thereof is five in FIG. 18), each which outside diameter is made reduced for the direction as shown by the arrow B of the direction of the axis center P1 of the main pillar portion 10. A plurality of the main pillar portion pieces 60 are unitedly formed in series in the directions as shown by the arrows A and B. That is, at the outer peripheral face 10i side of the main pillar portion 10 of the hub 9, a plurality of the projecting folds 61 formed by a plurality of the main pillar portion pieces 60 are annularly provided.

Therefore, the main pillar portion 10 of the hub 9 is inserted into the hub insertion hole 4b, thereby a plurality of the fold portions 61 of the main pillar portion 10 contact and engage with the inner peripheral face 7a of the hub insertion hole 4b with a predetermined seal pressure. The gap space 49 is formed between the inner peripheral face 7a of the hub insertion hole 4b and the main pillar portion 10 excluding a plurality of the fold portions 61.

The main pillar portion 10 is inserted into the hub insertion hole 4b in the direction as shown by the arrow B from the hole 8a of the end wall 8, and in case of the insertion, the hub 9 can be smoothly inserted into the hub insertion hole 4b since the fold portion 61 is formed tapering in the direction as shown by the arrow B. In addition, since the main pillar portion 10 is easily inserted into the hub insertion hole 4b by the tapered fold portions 61, this structure is applicable to the syringe body 2 having no slit 50 in the hub insertion hole 4b as well as the syringe body 2 having slits 50 in the hub insertion hole 4b.

In the method of assembling the syringe assembly 1 which is comprised in such a manner that the hub body 90 is inserted into the hub insertion hole 4b from the hole 8a side of the end wall 8, of the above-mentioned embodiments, the piston 29 is inserted into the syringe body 2, the hub 9 is inserted into the syringe body 2, and the needle 26 is inserted into and contacted with the hub 9. However, in the method of assembling the piston 29 is inserted into the syringe body 2, and after that, the hub 9 inserted the needle 26 therein in advance may be inserted into the syringe body 2. In this case, the syringe body 2 and the hub 9 attached the needle 26 thereto can be independently stored till just before using, and in use, a doctor and the like can use as a syringe assembly by inserting the hub 9 into the syringe 2, and various kinds of needles can be selectedly used for one syringe. As a result, the syringe body 2 and the hub 9 can be used for various purposes.

The present invention has been explained on the basis of the embodiments presented herein. However, the embodiments which are described in the present specification are illustrative and not limiting. The scope of the invention is designated by the accompanying claims and is not restricted by the descriptions of the specific embodiments. Accordingly, all the transformations and changes belonging to the claims are included in the scope Of the present invention.

I claim:

1. A syringe assembly comprising:

a syringe body having first and second ends and a central longitudinal axis, the syringe body forming an axial space to contain an injection medium;

a piston slidably received in the syringe body;

a holding member installation hole cylindrically formed at the first end of said syringe body;

a needle holding member adapted to connect with a needle, the needle holding member attachably and detachably received in said holding member installation hole, said needle holding member having a main body in the shape of a cylinder which can be linearly inserted into said holding member installation hole by selective application of linear force in one of a first direction substantially parallel to the longitudinal axis of said syringe body and a second direction opposite said first direction, and which can be linearly pulled out of said holding member installation hole into said syringe body by application of linear force in said second direction;

a seal portion in the shape of a projection having a first width in the longitudinal direction of said main body, the projection annularly formed at an outer peripheral portion of said main body;

member side engagement means provided with said main body so as to engage with said piston; and a member seal portion in the shape of a groove having a second width narrower than said first width in the longitudinal direction of said syringe body, the groove annularly formed at an inner peripheral face of said holding member installation hole of said syringe body, wherein said projection of said seal portion of said main body contacts and engages with said groove of said member seal portion with a predetermined contact pressure.

2. A syringe assembly comprising:

a syringe body having first and second ends and a central longitudinal axis, the syringe body forming an axial space to contain an injection medium;

a piston slidably received in the syringe body;

a holding member installation hole cylindrically formed at the first end of said syringe body;

a needle holding member adapted to connect with a needle, the needle holding member attachably and detachably received in said holding member installation hole, said needle holding member having a main body in the shape of a cylinder which can be linearly inserted into said holding member installation hole by selective application of linear force in one of a first direction substantially parallel to the longitudinal axis of said syringe body and a second direction opposite said first direction, and which can be linearly pulled out of said holding member installation hole into said syringe body by application of linear force in said second direction;

a seal portion in the shape of a groove having a first width in the longitudinal direction of said main body, the groove annularly formed at an outer peripheral portion of said main body;

member side engagement means provided with said main body so as to engage with said piston; and a member seal portion in the shape of a projection having a second width broader than said first width in the longitudinal direction of said syringe body, the projection annularly formed at an inner peripheral face of said holding member installation hole of said syringe body, wherein said groove of said seal portion of said main body contacts and engages with said projection of said member seal portion with a predetermined contact pressure.

3. The syringe assembly as set forth in claim 1 or 2, werein said piston comprises a piston body, the piston body being bendable and having a first portion pressable against a medical liquid received in the syringe body and a second portion to operate the piston.

4. The syringe assembly as set forth in claim 3, wherein a piston stopper is formed in said syringe body to retain said first portion of said piston within said syringe body.

5. The syringe assembly as set forth in claim 4, wherein a notch is formed on said piston body of said piston.

6. The syringe assembly as set forth in claim 5, wherein said notch is located on the piston body to be positioned at an end of said syringe body when said piston abuts said piston stopper.

7. The syringe assembly as set forth in claim 3, wherein a notch is formed on said piston body of said piston.

8. The syringe assembly as set forth in claims 1 or 2, wherein said holding member installation hole is a hub installation hole, and said needle holding member is a hub for a syringe assembly in which a needle can be directly installed.

9. The syringe assembly as set forth in claim 8, wherein a needle is installed in said main body.

10. The syringe assembly as set forth in claims 1 or 2, said holding member installation hole has a needle guide hole side, and said main body can be installed in said holding member installation hole from said needle guide hole side.

11. A method of assembling a syringe assembly comprising:

providing a syringe comprising a piston, a needle holding member and a syringe body with a needle side and a piston insertion side;

inserting said piston into said syringe;

inserting said needle holding member into a holding member installation hole in the syringe body from the needle side of said syringe body; and applying linear force to said needle holding a member to elastically engage a seal portion of said needle holding member and a member seal portion of said holding member installation hole and to form a seal between said seal portion and said member seal portion by engaging annular protrusion on one of the needle holding member and the syringe body, the protrusion having a relatively larger width in a longitudinal direction, into an annular groove in the other of said needle holding member and said syringe body, the annular groove having a relatively smaller width than the protrusion in said longitudinal direction.

12. The method of claim 11, wherein the syringe body has a needle guide hole, and further comprising forming at least one slit at a periphery of said syringe body in communication with said needle guide hole; and inserting said needle holding member into said holding member installation hole through said slit.

13. A method of assembling a syringe assembly comprising:

providing a syringe comprising a piston, a needle holding member aid a syringe body with a needle side and a piston insertion side;

inserting said needle holding member into a holding member installation hole in the syringe body from the piston insertion side;

applying linear force to said needle holding member to elastically engage a seal portion of said needle holding member and a member seal portion formed in said holding member installation hole and to form a said seal portion and said member seal portion by engaging an annular protrusion on one of the needle holding member and the syringe body, the protrusion having a relatively larger width in a longitudinal direction, into an annular groove in other of said needle holding member and said syringe body, the annular groove having a relatively smaller width than the protrusion in said longitudinal direction; and inserting said piston into said syringe.

14. A syringe assembly comprising:

a syringe body having first and second ends and a central longitudinal axis, the syringe body forming an axial space to contain an injection medium;

a piston slidably received in the syringe body;

a holding member installation hole cylindrically formed at the first end of said syringe body;

a needle holding member adapted to connect with a needle, the needle holding member attachably and detachably received in said holding member installation hole, said needle holding member having a main body in the shape of a cylinder which can be linearly inserted into said holding member installation hole by selective application of linear force in one of a first direction substantially parallel to the longitudinal axis of said syringe body and a second direction opposite said first direction, and which can be linearly pulled out of said holding member installation hole into said syringe body by application of linear force in said second direction;

a seal portion in the shape of a projection having a first width in the longitudinal direction of said main body, the projection annularly formed at an outer peripheral portion of said main body;

member side engagement means provided with said main body so as to engage with said piston; and a member seal portion in the shape of a groove having a second width narrower than said first width in the longitudinal direction of said syringe body, the groove annularly formed at an inner peripheral face of said holding member installation hole of said syringe body, wherein said projection of said seal portion of said main body contacts and engages with said groove of said member seal portion with a predetermined contact pressure;

wherein said holding member installation hole is a hub installation hole, and said needle holding member is a hub for a syringe assembly in which a needle can be directly installed; and wherein at least one slit is formed at a periphery of said syringe body and communicates with said hub installation hole.

15. A syringe assembly comprising:

a syringe body having first and second ends and a central longitudinal axis, the syringe body forming an axial space to contain an injection medium;

a piston slidably received in the syringe body;

a holding member installation hole cylindrically formed at the first end of said syringe body;

a needle holding member adapted to connect with a needle, the needle holding member attachably and detachably received in said holding member installation hole, said needle holding member having a main body in the shape of a cylinder which can be linearly inserted into said holding member installation hole by selective application of linear force in one of a first direction substantially parallel to the longitudinal axis of said syringe body and a second direction opposite said first direction, and which can be linearly pulled out of said holding member installation hole into said syringe body by application of linear force in said second direction;

a seal portion in the shape of a groove having a first width in the longitudinal direction of said main body, the groove annularly formed at an outer peripheral portion of said main body;

member side engagement means provided with said main body so as to engage with said piston; and a member seal portion in the shape of a projection having a second width broader than said first width in the longitudinal direction of said syringe body, the projection annularly formed at an inner peripheral face of said holding member installation hole of said syringe body, wherein said groove of said seal portion of said main body contacts and engages with said projection of said member seal portion with a predetermined contact pressure;

wherein said holding member installation hole is a hub installation hole, and said needle holding member is a hub for a syringe assembly in which a needle can be directly installed; and wherein at least one slit is formed at a periphery of said syringe body and communicates with said hub installation hole.

* * * * *

UNITED STATES PATENT AND TRADEMARK OFFICE
CERTIFICATE OF CORRECTION

PATENT NO. : 5,772,687
DATED : June 30, 1998
INVENTOR(S) : Yoshikuni Saito

It is certified that error appears in the above-indentified patent and that said Letters Patent is hereby corrected as shown below:

Column 18, line 24, delete "1 ha" and substitute therefor --11a--.

Column 18, line 31, delete "hla" and substitute therefor --11a--.

Column 19, line 29, delete "10ion" and substitute therefor --10i on--.

Claim 11, column 38, line 59, after the word "engaging" insert --an--.

Claim 13, column 39, line 17, after "a", insert --seal between--.

Signed and Sealed this

Tenth Day of November 1998

Attest:

BRUCE LEHMAN

*Attesting Officer*  *Commissioner of Patents and Trademarks*